United States Patent
Rackham et al.

(10) Patent No.: US 7,888,293 B2
(45) Date of Patent: Feb. 15, 2011

(54) COMPOSITIONS AND METHODS RELATING TO ORTHOGONAL RIBOSOME MRNA PAIRS

(75) Inventors: Oliver Rackham, Western Australia (AU); Jason W. Chin, Cambridge (GB)

(73) Assignee: Medical Research Council, London (GB)

( * ) Notice: Subject to any disclaimer, the term of this patent is extended or adjusted under 35 U.S.C. 154(b) by 52 days.

(21) Appl. No.: 11/982,877

(22) Filed: Nov. 6, 2007

(65) Prior Publication Data
US 2009/0048434 A1 Feb. 19, 2009

Related U.S. Application Data

(63) Continuation of application No. PCT/GB2006/002637, filed on Jul. 14, 2006.

(60) Provisional application No. 60/699,936, filed on Jul. 15, 2005.

(51) Int. Cl.
C07H 21/02 (2006.01)
C07K 2/00 (2006.01)
C12N 1/06 (2006.01)
C12N 15/63 (2006.01)
C12N 9/96 (2006.01)
C12P 21/02 (2006.01)
C40B 30/06 (2006.01)

(52) U.S. Cl. .................. 506/26; 536/23.1; 435/188; 435/252.3; 435/320.1; 435/69.1; 506/10; 530/300

(58) Field of Classification Search ............... None
See application file for complete search history.

(56) References Cited

U.S. PATENT DOCUMENTS
2003/0108885 A1 6/2003 Schultz et al.

FOREIGN PATENT DOCUMENTS
WO PCT/US94/05601 12/1994

OTHER PUBLICATIONS

Lee (Nov. 2001) The Journal of Nutrition vol. 131 p. 2994S.*
Erikson (Mar. 21, 2004) Nature Biotechnology vol. 22 p. 455.*
Peck (Feb. 2000) Molecular Microbiology vol. 35 p. 667.*
Yusupova (Jul. 27, 2001) Cell vol. 106 p. 233.*
Lee K. et al: Genetic Analysis of the Shine-Dalgarno Interaction: Selection of Alternative Functional MRNA-RRNA Combinations: RNA, Cold Spring Harbor Laboratory Press, Woodbury NY, US, vol. 2, No. 12, Dec. 1996, pp. 1270-1285.
Hui A. et al.: "Specialized ribosome system: preferential translation of a single mRNA species by a subpopulation of mutated ribosomes in *Escherichia coli*." Proceedings of the National Academy of Sciences of the United States of America, Jul. 1987, vol. 84, No. 14, Jul. 1987 pp. 4762-4766.

* cited by examiner

Primary Examiner—Jeffrey S Lundgren
Assistant Examiner—Christian Boesen
(74) Attorney, Agent, or Firm—Edwards Angell Palmer & Dodge LLP; Kathleen Williams; Amy DeCloux

(57) ABSTRACT

Orthogonal ribosome orthogonal mRNA pairs are provided, as are methods for their selection involving a novel positive-negative selection approach, and methods for their use. Also provided are cellular logic circuits involving orthogonal ribosomes.

12 Claims, 11 Drawing Sheets

```
                    -13      -7
                     |        |
classic SD   5'  UUUCAUAGGAGGCCGCAAAUG  3'
16S rRNA         3'  AUUCCUCCACUA.....CGGUGGCC  5'
                     |         |       |       |
                    1542      1531    726     719 mRNAlib      UUUCANNNNNNNCCGCAAAUG
rRNAlib         AUNNNNNNNACUA.....CGGNNGCC
```

```
           -13       -7             No.
classic SD  5' UUUCAUAGGAGGCCGCAAAUG 3'
mRNAlib        UUUCANNNNNNNNCCGCAAAUG
mRNA-A         UUUCACACCAC-CCGCAAAUG    16
mRNA-B         UUUCACAACUGCCCGCAAAUG    26
mRNA-C         UUUCACAUCCCUCCGCAAAUG     6
mRNA-D         UUUCAUCCCU--CCGCAAAUG     3

719    726  1531       1542
16S rRNA    3' CCGGUUGGC....AUCACCUCCUUA 5'
rRNAlib        CCGNNUGGC....AUCANNNNNNUA
rRNA-1         CCGAGUGGC....AUCAAGUGGUUA  5
rRNA-2         CCGCGUGGC....AUCACUGUGGUA  3
rRNA-3         CCGCAUGGC....AUCAUUGUGGUA  4
rRNA-4         CCGGUUGGC....AUCAUUGUGGUA  4
rRNA-5         CCGACUGGC....AUCAAUGCAGUA  3
rRNA-6         CCGACUGGC....AUCAUUGCAGUA 16
rRNA-7         CCGCGUGGC....AUCAUCGCAGUA  3
rRNA-8         CCGCAUGGC....AUCACCGCAGUA  4
rRNA-9         CCGCAUGGC....AUCAUGGGAUUA  6
rRNA-10        CCGGUUGGC....AUCAUGGGAUUA  3
```

FIG. 4a

| Clone | mRNA·rRNA pair | No. | IC50mRNA | IC50pair |
|---|---|---|---|---|
| classic SD | 5' UUUCAUAGGAGGCCGCAAAUG 3'<br>3' AUUCCUCCACUA.....CGGUGGCC 5' | — | — | 150 |
| 16S rRNA | 1542      1531     726    719 | | | |
| mRNAlib<br>rRNAlib | UUUCANNNNNNNNCCGCAAAUG<br>AUNNNNNNNACUA.....CGGNNGCC | — | — | — |
| A1 | UUUCACACCACCCGCAAAUG<br>AUUGGUGAACUA.....CGGGAGCC | 5 | 10 | 200 |
| A2 | UUUCACACCACCCGCAAAUG<br>AUGGUGUCACUA....CGGGCGCC | 3 | 10 | 200 |
| A3 | UUUCACACCACCCGCAAAUG<br>AUGGUGUUACUA....CGGACGCC | 4 | 10 | 200 |
| A4 | UUUCACACCACCCGCAAAUG<br>AUGGUGUUACUA....CGGUGGCC | 4 | 10 | 200 |
| B5 | UUUCACAACUGCCCGCAAAUG<br>AUGACGUAACUA...CGGCAGCC | 3 | 10 | 150 |
| B6 | UUUCACAACUGCCCGCAAAUG<br>AUGACGUUACUA...CGGCAGCC | 16 | 10 | 150 |
| B7 | UUUCACAACUGCCCGCAAAUG<br>AUGACGCUACUA...CGGGCGCC | 3 | 10 | 150 |
| B8 | UUUCACAACUGCCCGCAAAUG<br>AUGACGCCACUA...CGGACGCC | 4 | 10 | 150 |
| C9 | UUUCACAUCCCUCCGCAAAUG<br>AUUAGGGUACUA.....CGGACGCC | 6 | 10 | 150 |
| D10 | UUUCAUCCCUCCGCAAAUG<br>AUUAGGGUACUA.......CGGUGGCC | 3 | 10 | 150 |

FIG. 4b

COMPOSITIONS AND METHODS RELATING TO ORTHOGONAL RIBOSOME MRNA PAIRS

This is a continuation patent application that claims priority to PCT application number PCT/GB2006/002637, filed on Jul. 14, 2006, which claims the benefit of provisional application No. 60/699,936, filed Jul. 15, 2005, the entirety of which are herein incorporated by reference.

FIELD OF THE INVENTION

The invention relates to the field of protein translation biochemistry. More specifically, the invention relates to orthogonal ribosome orthogonal mRNA pairs, methods of selecting them and their use.

BACKGROUND OF THE INVENTION

The synthesis of networks of molecules to perform well-defined functions in cells is a central aim of synthetic biology (Gibbs, W. W., *Sci Am* 290, 74-81 (2004), Brent, R, *Nat Biotechnol* 22, 1211-1214 (2004)). Networks have been assembled, or evolved, from a handful of well-characterized natural transcription factors and their binding sites (Basu, S., Gerchman, Y., Collins, C. H., Arnold, F. H. & Weiss, R., *Nature* 434, 1130-1134 (2005), Elowitz, M. B. & Leibler, S., *Nature* 403, 335-338 (2000), Gardner, T. S., Cantor, C. R. & Collins, J. J., *Nature* 403, 339-342 (2000), Guet, C. C., Elowitz, M. B., Hsing, W. & Leibler, S., *Science* 296, 1466-1470 (2002), Kaern, M., Blake, W. J. & Collins, J. J., *Annu Rev Biomed Eng* 5, 179-206 (2003), Kobayashi, H. et al., *Proc Natl Acad Sci USA* 101, 8414-8419 (2004), Yokobayashi, Y., Weiss, R. & Arnold, F. H., *Proc Natl Acad Sci USA* 99, 16587-16591 (2002), You, L., Cox, R. S., 3rd, Weiss, R. & Arnold, F. H., *Nature* 428, 868-871 (2004)), to create cellular oscillators, toggle switches and logic functions, and to create novel modes of cell-cell communication and cell pattern formation.

Modified ribosomes with an altered or narrowed scope of mRNA substrates have been examined for possible use in expanding the genetic code and for the purposes of post-transcriptional gene regulation. Previous work has described "specialized ribosomes" (Hui, A. S., Eaton, D. H. & de Boer, H. A., *EMBO J.* 7, 4383-4388 (1988), Hui, A., Jhurani, P. & de Boer, H. A., *Methods Enzymol* 153, 432-452 (1987), Hui, A. & de Boer, H. A., *Proc Natl Acad Sci USA* 84, 4762-4766 (1987)) that bear three mutations in the SD sequence and translate mRNAs bearing complementary mutations in the ASD.

Lee et al. describe experiments in which random mutations were simultaneously introduced to the rRNA binding sequence (SD) on chloramphenicol acetyltransferase mRNA and the complementary message-binding sequence of the *E. coli* 16S ASD (Lee et al., 1996, RNA 2: 1270-1285). Alternate SD sequences that rely to varying degrees for their translation on wild-type ribosomes were isolated from a collection of ASD and SD mutants (Lee, K., Holland-Staley, C. A. & Cunningham, P. R., *RNA* 2, 1270-1285 (1996).

SUMMARY OF THE INVENTION

Orthogonal ribosome orthogonal mRNA pairs are provided, as are methods for their selection involving a novel positive-negative selection approach. Also provided are cellular logic circuits involving orthogonal ribosomes.

The positive-negative selection approach uses a fusion polypeptide comprising a positive selectable marker polypeptide fused to a negative selectable marker in a manner that permits each constituent of the fusion polypeptide to retain its selectable marker function. A library of mRNAs having diversified or mutated ribosome binding sites operably linked to the positive-negative selectable marker fusion polypeptide is selected using the negative selectable marker to remove mRNAs that are substrates for the wild-type ribosome, thereby enriching for mutant mRNAs that are not substrates for the wild-type ribosome. Cells expressing mutant mRNAs enriched by the negative selection are then transformed with a second library encoding small subunit rRNA molecules that are mutated in a region comprising sequence that interacts with mRNA at the ribosome binding site. The cells are then selected for expression of the positive selectable marker, which enriches for ribosomes comprising mutant small subunit rRNAs that are able to efficiently translate the mutant mRNAs selected in the negative selection. Resulting mRNA rRNA/ribosome pairs are orthogonal. The orthogonal ribosome members of the pairs are not toxic when expressed in a cell and only efficiently translate a cognate orthogonal mRNA. The orthogonal pairs can, for example, provide sensitively regulated novel operators to regulate cell function.

Also provided are fusion polypeptides comprising a positive selectable marker polypeptide and a negative selectable marker polypeptide. The expression of the fusion polypeptide permits cell survival in the presence of a positive selectable marker and renders cells sensitive to killing by the negative selectable marker. Vectors encoding such fusion polypeptides, including, but not limited to vectors in which the coding sequences for the fusion polypeptide are operably linked to diversified ribosome binding sites are also provided, as are host cells comprising and/or expressing such vectors. The positive-negative selection approach can be applied to the selection of additional control elements, including, for example, altered transcriptional or translational control elements, such as riboswitches, riboregulators, transcriptional regulators, transcription factors, RNA polymerases and promoter sequences.

Also provided are methods of making a polypeptide of interest using orthogonal mRNA•orthogonal ribosome pairs as described herein. Such methods involve introducing nucleic acid encoding such a pair to a cell, where the orthogonal mRNA encodes the polypeptide of interest. The translation of the orthogonal mRNA by the orthogonal ribosome (containing the orthogonal rRNA) results in production of the polypeptide of interest. Polypeptides produced in cells encoding orthogonal mRNA•orthogonal ribosome pairs can include unnatural amino acids.

Also provided are Boolean logic circuits programmed in cells using one or more orthogonal ribosome orthogonal mRNA pairs such as those described herein.

Figure 1:
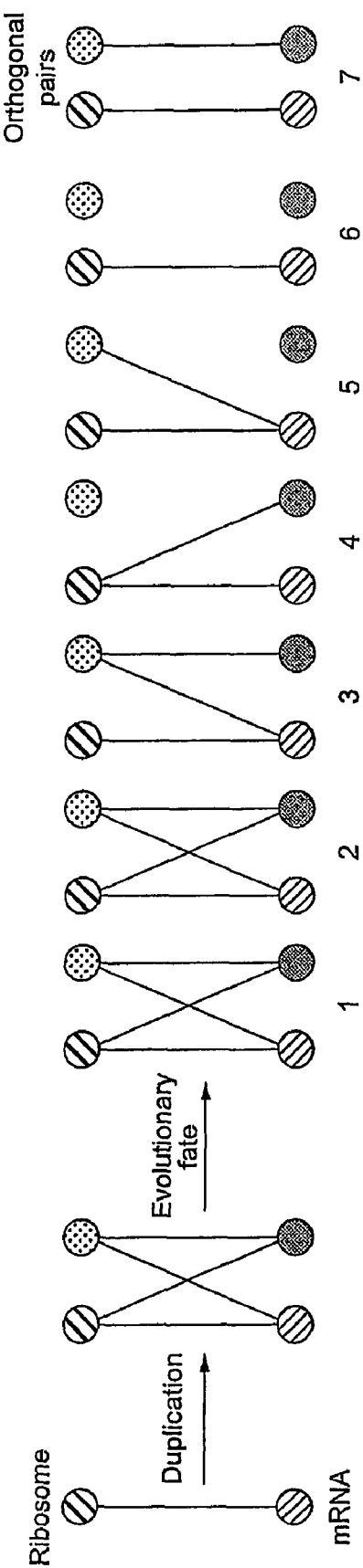
FIG. 1. Creating Novel Ribosome mRNA Interactions.

The potential fates of a pair of duplicated interacting molecules. The progenitor ribosome (black circle) interacts (black line) with cognate progenitor mRNA (cross-hatched circle). The diverse cellular ribosome mRNA interactions are represented by this single interaction for simplicity. Duplication initially leads to a second copy of the mRNA (grey circle), which is a substrate for the progenitor ribosome and a second ribosome (checkerboard circle) that translates the progenitor, mRNA. Numerous evolutionary fates may befall the duplicated copies. (1) Subsequent mutations do not alter the specificity of the mRNAs or ribosomes. (2) The duplicated ribosome evolves to translate the duplicated and altered mRNA, but no longer translates endogenous mRNAs. (3) The duplicated mRNA mutates so that it is no longer a substrate for the progenitor ribosome and the duplicated ribosome mutates so that it promiscuously translates both the progenitor and duplicated mRNA. (4) The duplicate ribosome accrues mutations that inactivate it, and the duplicate mRNA remains a substrate for the progenitor ribosome. (5) The duplicate mRNA accrues mutations, and the duplicate ribosome continues to translate progenitor mRNAs. (6) The duplicate ribosome and mRNA are both inactive. (7) The duplicate mRNA accrues mutations so that it is no longer a substrate for the progenitor ribosome. The duplicate ribosome accrues mutations so that it no longer translates the progenitor mRNA, but does translate the duplicate mRNA. Such ribosome mRNA pair are described as orthogonal. Evolutionary choices in which the progenitor molecules also evolve are not considered here.

FIG. 2. Positive and Negative Selections on Active and Inactive Ribosome mRNA Pairs.

(a) Schematic of the selection. (b) CAT an UPRT are functionally expressed from cat-upp and the positive and negative selections each have a wide dynamic range.

FIG. 3. The Design of Ribosome and mRNA Libraries for the Selection of Orthogonal Pairs.

(a) The classic SD ASD interaction (TOP) and the nucleotides randomized in mRNAlib and rRNAlib (BOTTOM) (See SEQ ID NOs 114-119). (b) The SD ASD interaction helix in the ribosome. The molecular details are modeled from 5 Å structures (PDB accession numbers 1JGO and 1YL4. Image created using PyMOL: www.pymol.org).

FIG. 4. Characterization of Potentially O-ribosome O-mRNA Pairs.

(a) The sequences of mRNAlib and rRNAlib clones surviving both steps of the selection. (See SEQ ID NOs 48-83). The number (No.) of occurrences of each sequence in 51 clones is indicated to the right of the sequence. (b) The ribosome mRNA pairs isolated (See SEQ ID NOs 84-113). Pairs are separated into classes, on the basis of predicted base-pairing, by grey lines. (c) Cells transformed with mutant ribosomes do not affect growth. Each curve is the average of at least three independent trials and the error bars represent the standard error. (d) Selected ribosomes do not measurably translate endogenous proteins. Cells containing the indicated rRNA were co-transformed with plasmids in which the cat-upp fusion was deleted (Δ, or with the cognate mRNAlib clone (encoding cat-upp). Spectinomycin was added to cells to inhibit protein synthesis by the endogenous ribosome, but not ribosomes using plasmid encoded rRNA. (Rasmussen, U. B., Mygind, B. & Nygaard, P., *Biochim Biophys Acta* 881, 268-275 (1986)). $^{35}$S methionine was added to visualize subsequent protein synthesis. Equivalent $OD_{600}$s of cells were lysed and proteins separated by SDS-PAGE.

FIG. 5. (a) Synthesis of a Post-transcriptionally Regulated Boolean AND Function Using Orthogonal Ribosomes.

The output of the gate is β-galactosidase activity, which leads to a brown color in the presence of S-gal. (b) The chloramphenicol resistance of cognate and non-cognate orthogonal ribosome mRNA pairs. (c) The predicted (left) and observed (right) network of interactions between cognate and non-cognate ribosomes and mRNAs.

Figure 6:
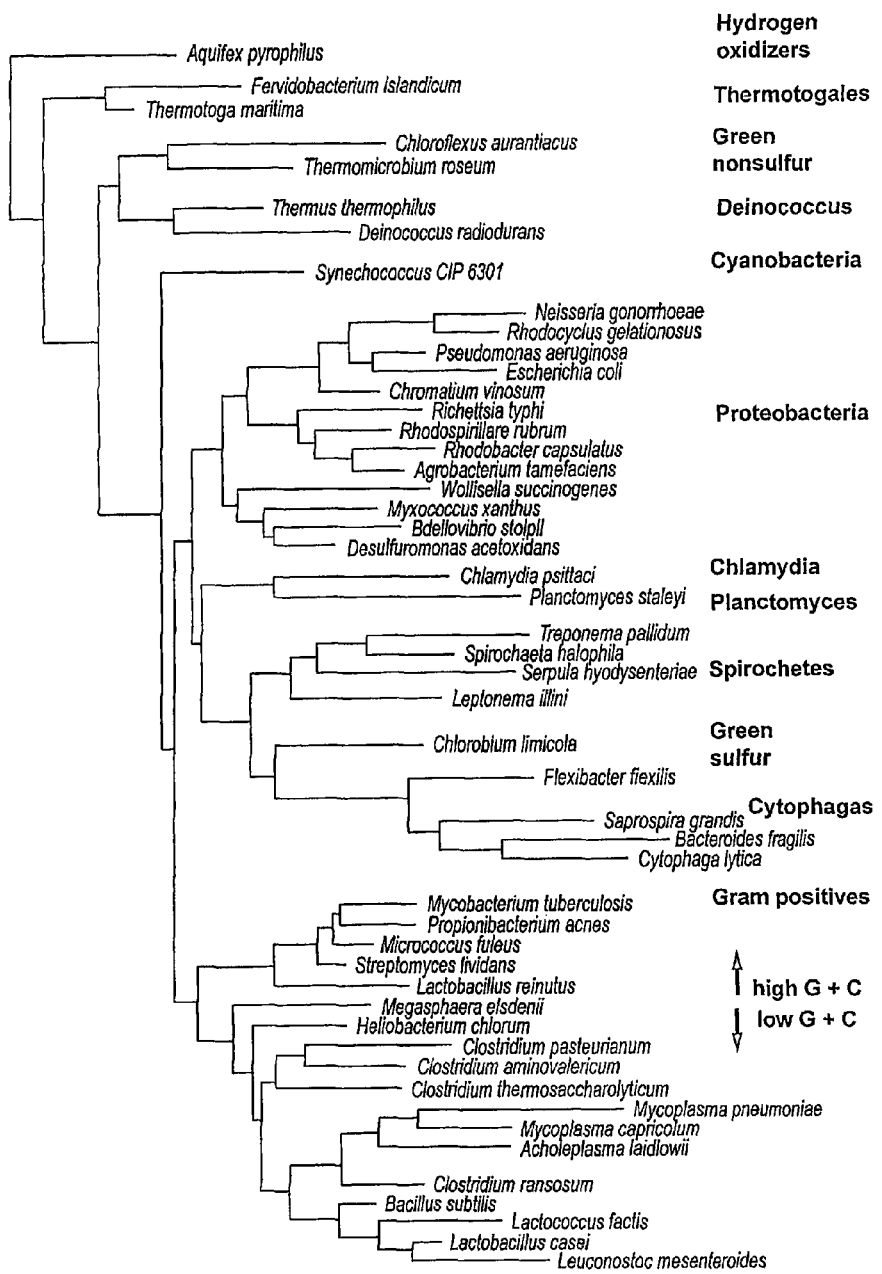

FIG. 6. An example of a bacterial phylogenetic tree based on 16S rRNA sequences.

Figures 7A, 7B:
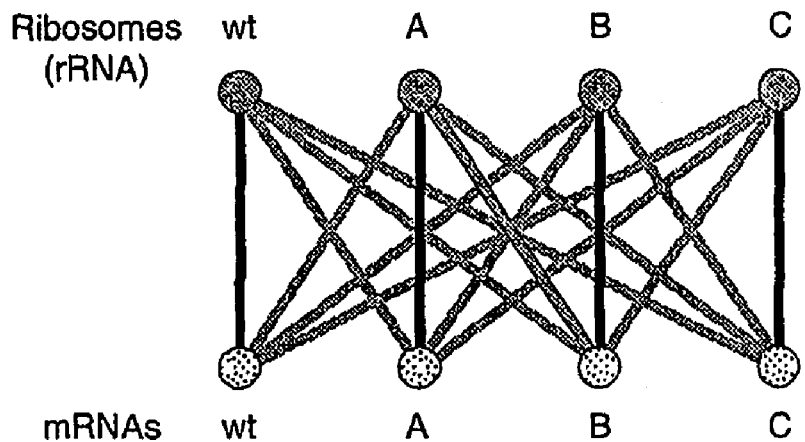

FIG. 7. Orthogonal ribosome-orthogonal mRNA pairs and their network of specificities. (a) The sequence of rRNA that interacts with mRNA is shown (wt is wild-type). WT mRNA and WT 16S rRNA are SEQ ID NO:114 and SEQ ID NO:116, respectively. Mutations in O-mRNAs and O-rRNAs are shown. O-mRNA-A and O-rRNA-A are SEQ ID NO:124 and SEQ ID NO:125, respectively. O-mRNA-B and O-rRNA-B are SEQ ID NO:126 and SEQ ID NO:127, respectively. O-mRNA-C and O-rRNA-C are SEQ ID NO:128 and SEQ ID NO:129, respectively. (b) Pairwise ribosome.cndot.mRNA interaction strengths are indicated by greyscale intensity.

FIG. 8. Combinatorial logic with orthogonal ribosomes. (a) The fluorescence generated as a function of ribosome inputs for the AND gate. Fluorescence is normalized for cell density and time of incubation, as detailed herein below. Error bars represent the standard error of at least three independent trials (b) Each state of the AND gate. Black lines indicate functional connections, while grey lines indicate components that are insulated from each other. (c,d) As for (a) and (b) but for the OR gate.

Figure 9:
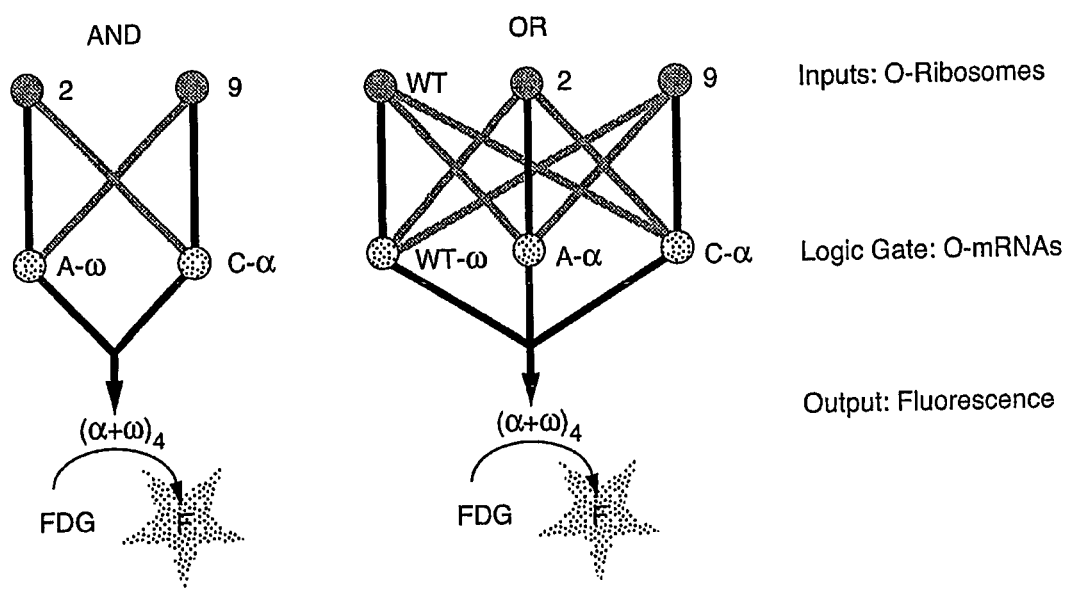

FIG. 9. Schematic of networks of Boolean AND and OR logic gates described herein.

DESCRIPTION

Definitions

As the term "orthogonal" is used herein, it refers to an mRNA rRNA pair (or an mRNA ribosome-comprising-an-rRNA pair) in which the mRNA is efficiently translated by a ribosome comprising the rRNA of the pair, but not by an endogenous ribosome, and in which the ribosome comprising the rRNA efficiently translates the mRNA of the pair, but not endogenous mRNAs. In this sense, the members of the pair are well separated from other mRNAs and rRNAs/ribosomes, in that other mRNAs can be translated by other (e.g., endogenous) ribosomes and other ribosomes can translate a number of different mRNAs. Thus, an "orthogonal mRNA orthogonal rRNA pair" or "O-mRNA O-rRNA pair" (or O-mRNA O-ribosome pair) is one in which the mRNA is efficiently translated by a ribosome containing the rRNA of the pair but not by an endogenous ribosome, and in which a ribosome comprising the rRNA efficiently translates the mRNA of the pair but not endogenous mRNA. In this relationship, the members of the O-mRNA O-rRNA pair are said to be "cognate" to each other. For simplicity, a ribosome comprising an orthogonal rRNA is referred to herein as an "orthogonal ribosome," and an orthogonal ribosome will efficiently translate only a cognate orthogonal mRNA.

As used herein, the term "mRNA" when used in the context of an O-mRNA O-ribosome pair refers to an mRNA that comprises a ribosome binding site (particularly the sequence from the AUG initiation codon upstream to −13 relative to the AUG) that efficiently mediates the initiation of translation by the O-ribosome, but not by a wild-type ribosome. The remainder of the mRNA can vary, such that placing the coding sequence for any protein downstream of that ribosome binding site will result in an mRNA that is translated efficiently by the orthogonal ribosome, but not by an endogenous ribosome.

As used herein, the term "rRNA" when used in the context of an O-mRNA O-ribosome pair refers to a small ribosomal subunit rRNA mutated in the 3' sequences that interact with mRNA during the initiation of translation. The mutation(s) is/are such that the rRNA is an orthogonal rRNA, and a ribosome containing it is an orthogonal ribosome, i.e., it efficiently translates only a cognate orthogonal mRNA. The primary, secondary and tertiary structures of wild-type small ribosomal subunit rRNAs are very well known, as are the functions of the various conserved structures (stems-loops, hairpins, hinges, etc.). Mutations outside the 3' sequences that interact with the mRNA during the initiation of translation are permissible in an O-rRNA as described herein to the extent that the O-rRNA remains orthogonal and that the mutation(s) maintain(s) the function of the ribosome in translation (translation function is maintained if the ribosome has at least 80%, and preferably at least 90%, 95% or even more preferably 100% of the activity of a corresponding ribosome with wild-type sequences outside of the 3' sequences that interact with the mRNA during the initiation of translation). That is, mutations outside the 3' sequences that interact with mRNA during translation initiation should generally be conservative or compensatory mutations that maintain the secondary and tertiary structure of the rRNA within the ribosome and maintain the function of the rRNA and the ribosome containing it.

The expression of an "O-rRNA" in a cell, as the term is used herein, is not toxic to the cell. Toxicity is measured by cell death, or alternatively, by a slowing in the growth rate by 80% or more relative to a cell that does not express the "O-mRNA." Expression of an O-rRNA will preferably slow growth by less than 50%, preferably less than 25%, more preferably less than 10%, and more preferably still, not at all, relative to the growth of similar cells lacking the O-rRNA.

As used herein, the terms "efficiently translates" and "efficiently mediates translation" mean that a given O-mRNA is translated by a cognate O-ribosome at least 80% as efficiently, and preferably at least 90%, 95% or even 100% as efficiently as an mRNA comprising a wild-type ribosome binding sequence is translated by a wild-type ribosome in the same cell or cell type. As a gauge, for example, in *E. coli* one may evaluate translation efficiency relative to the translation of an mRNA having a wild-type *E. coli* β-galactosidase ribosome binding sequence. In eukaryotic cells, one may use as a gauge, for example, an mRNA having a wild-type β-actin ribosome binding sequence.

As used herein, the term "corresponding to" when used in reference to nucleotide sequence means that a given sequence in one molecule, e.g., in a 16S rRNA, is in the same position in another molecule, e.g., a 16S rRNA from another species. By "in the same position" is meant that the "corresponding" sequences are aligned with each other when aligned using the BLAST sequence alignment algorithm "BLAST 2 Sequences" described by Tatusova and Madden (1999, "Blast 2 sequences—a new tool for comparing protein and nucleotide sequences", FEMS Microbiol. Lett. 174:247-250) and available from the U.S. National Center for Biotechnology Information (NCBI). To avoid any doubt, the BLAST version 2.2.11 (available for use on the NCBI website or, alternatively, available for download from that site) is used, with default parameters as follows: program, blastn; reward for a match, 1; penalty for a mismatch, −2; open gap and extend gap penalties 5 and 2, respectively; gap×dropoff, 50; expect 10.0; word size 11; and filter on.

As used herein, the term "selectable marker" refers to a gene sequence that permits selection for cells in a population that encode and express that gene sequence by the addition of a corresponding selection agent.

As used herein, a "positive selectable marker" is a selectable marker in which the expression of the marker is necessary for the survival of a cell in the presence of a selection agent. A non-limiting example of a positive selectable marker is antibiotic resistance, in which the expression of a resistance gene in a cell renders the cell insensitive to specific growth retardation or killing with an antibiotic. A "corresponding" positive selection agent is an agent that kills cells or severely retards growth of cells lacking the positive selectable marker but does not kill cells expressing the positive selectable marker. A non-limiting example of a "corresponding" positive selectable agent is an antibiotic, e.g., ampicillin or chloramphenicol where the positive selectable marker is an antibiotic resistance gene, e.g., β-lactamase or chloramphenicol acetyltransferase, respectively.

As used herein, a "negative selectable marker" is a selectable marker in which the expression of the marker renders a cell susceptible to killing or growth retardation with a selection agent. Non-limiting examples of negative selectable markers include thymidine kinase (selectable with gancyclovir), *B. subtilis* sacB (selectable with sucrose), and uracil phosphoribosyltransferase (selectable with 5-fluorouracil). A "corresponding" negative selection agent is an agent to which cells expressing the negative selectable marker become sensitive; thus, for example, gancyclovir "corresponds" to thymidine kinase, sucrose "corresponds" to sacB, and 5-fluorouracil "corresponds" to uracil phosphoribosyltransferase in the preceding examples.

As used herein, the term "chloramphenicol acetyltransferase" refers to an enzyme that catalyzes the acetylation of chloramphenicol which renders the chloramphenicol inactive for translation blockade and inactive for cell killing. Assays for measuring acetylation of chloramphenicol by chloramphenicol acetyltransferase are well known in the art.

As used herein, the term "growth retardation" means that in cells sensitive to such retardation, the doubling time of bacteria is at least two times as long as in insensitive bacteria, preferably at least three, four or five times or more longer, relative to cells that are not sensitive to the retardation. Over the time course of multiple doublings for an insensitive cell, the proportion of the population of insensitive cells will rapidly become dominant, e.g., 95%, 99% or more, relative to sensitive cells.

The term "uracil phosphoribosyltransferase" refers to an enzyme that catalyzes the phosphorylation of uracil to uridine monophosphate.

As used herein, "survival in the presence of chloramphenicol" means that a cell expressing chloramphenicol acetyltransferase will survive in medium containing chloramphenicol at a concentration in which 100% of cells that do not express chloramphenicol acetyltransferase are killed or severely growth retarded. "Severely" growth retarded means an increase in doubling time of 5 times or more relative to non-retarded growth.

As used herein, "sensitive to killing with 5-fluorouracil" means that all cells in a population expressing a CAT/UPRT fusion as described herein are killed at a concentration of 5-FU greater than or equal to 0.1 μg/ml.

As used herein, the term "region comprising sequence that interacts with mRNA at the ribosome binding site" refers to a region of sequence comprising the nucleotides near the 3' terminus of 16S rRNA that physically interact, e.g., by base pairing or other interaction, with mRNA during the initiation of translation. The "region" includes nucleotides that base pair or otherwise physically interact with nucleotides in mRNA at the ribosome binding site, and nucleotides within five nucleotides 5' or 3' of such nucleotides. Also included in this "region" are bases corresponding to nucleotides 722 and 723 of the *E. coli* 16S rRNA, which form a bulge proximal to the minor groove of the Shine-Dalgarno helix formed between the ribosome and mRNA.

As used herein, the term "diversified" means that individual members of a library will vary in sequence at a given site. Methods of introducing diversity are well known to those skilled in the art, and can introduce random or less than fully random diversity at a given site. By "fully random" is meant that a given nucleotide can be any of G, A, T, or C (or in RNA, any of G, A, U and C). By "less than fully random" is meant that a given site can be occupied by more than one different nucleotide, but not all of G, A, T (U in RNA) or C, for example where diversity permits either G or A, but not U or C, or permits G, A, or U but not C at a given site.

As used herein, the term "ribosome binding site" refers to the region of an mRNA that is bound by the ribosome at the initiation of translation. As defined herein, the "ribosome binding site" of prokaryotic mRNAs includes the Shine-Dalgarno consensus sequence and nucleotides −13 to +1 relative to the AUG initiation codon.

As used herein, the term "unnatural amino acid" refers to an amino acid other than the 20 amino acids that occur naturally in protein. Non-limiting examples include: a p-acetyl-L-phenylalanine, a p-iodo-L-phenylalanine, an O-methyl-L-tyrosine, a p-propargyloxyphenylalanine, a p-propargyl-phenylalanine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-bromophenylalanine, a p-amino-L-phenylalanine, an isopropyl-L-phenylalanine, an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or a combination thereof; an amino acid with a photoactivatable cross-linker; a spin-labeled amino acid; a fluorescent amino acid; a metal binding amino acid; a metal-containing amino acid; a radioactive amino acid; a photocaged and/or photoisomerizable amino acid; a biotin or biotin-analogue containing amino acid; a keto containing amino acid; an amino acid comprising polyethylene glycol or polyether; a heavy atom substituted amino acid; a chemically cleavable or photocleavable amino acid; an amino acid with an elongated side chain; an amino acid containing a toxic group; a sugar substituted amino acid; a carbon-linked sugar-containing amino acid; a redox-active amino acid; an α-hydroxy containing acid; an amino thio acid; an α, α disubstituted amino acid; a β-amino acid; a cyclic amino acid other than proline or histidine, and an aromatic amino acid other than phenylalanine, tyrosine or tryptophan.

As used herein, the term "logic circuit" refers to a set of interacting parameters with a read out that announces the state of the interacting parameters. For example, a "Boolean AND circuit" refers to a set of two entities or conditions, A and B, that must be present or satisfied to give read-out C. Read-out C is only given when conditions A AND B are satisfied. A "Boolean OR circuit" refers to a set of two entities or conditions A and B, and a read-out D. In the OR circuit, read-out D is given, for example, when A OR B are satisfied. Thus, if A OR B is satisfied, read-out D is given in the OR circuit. A "cellular" logic circuit is a logic circuit as defined herein in which the entities of the logic circuit necessary to provide a read-out are expressed in a living cell. As used herein, the term "cascade" refers to a series of logic circuits in which the result of one circuit is required as an element in a second circuit.

DETAILED DESCRIPTION

Synthetic biology aims for the ability to program cells with new functions. Simple oscillators, switches, logic functions, cell-cell communication and pattern forming circuits have been created, by the connection of a small set of natural transcription factors and their binding sites in different ways to create different networks of molecular interactions. However, the controlled synthesis of more complex synthetic networks and functions requires an expanded set of functional molecules with known molecular specificities.

Networks of molecular interactions in organisms have evolved to allow the increase in complexity from unicellular organisms to metazoans (Ohno, S., Springer-Verlag, Heidelberg, N.Y.; 1970), Taylor, J. S. & Raes, J., *Annu Rev Genet* 38, 615-643 (2004), Teichmann, S. A. & Babu, M. M., *Nat Genet* 36, 492-496 (2004)) through duplication of a progenitor gene followed by the acquisition of a novel function (neofunctionalization) in the duplicated copy. Described herein are processes that artificially mimic the natural process to produce orthogonal molecules: that is, molecules that can process information in parallel with their progenitors without cross-talk between the progenitors and the duplicated molecules. Using these processes, it is now possible to tailor the evolutionary fates of a pair of duplicated molecules from amongst the many natural fates to give a predetermined relationship between the duplicated molecules and the progenitor molecules from which they are derived (see, e.g., FIG. 1). This is exemplified herein by the generation of orthogonal ribosome orthogonal mRNA pairs that can process information in parallel with wild-type ribosomes and mRNA but that do not engage in cross-talk between the wild-type and orthogonal molecules.

The bacterial ribosome is a 2.5 MDa complex of rRNA and protein responsible for translation of mRNA into protein (The Ribosome, Vol. LXVI. (Cold Spring Harbor Laboratory Press, Cold Spring Harbor, N.Y.; 2001). The interaction between the mRNA and the 30S subunit of the ribosome is an early event in translation (Laursen, B. S., Sorensen, H. P., Mortensen, K. K. & Sperling-Petersen, H. U., *Microbiol Mol Biol Rev* 69, 101-123 (2005)), and several features of the mRNA are known to control the expression of a gene, including the first codon (Wikstrom, P. M., Lind, L. K., Berg, D. E. & Bjork, G. R., *J Mol Biol* 224, 949-966 (1992)), the ribosome-binding sequence (including the Shine Dalgarno (SD) sequence (Shine, J. & Dalgarno, L., *Biochem J* 141, 609-615 (1974), Steitz, J. A. & Jakes, K., *Proc Natl Acad Sci USA* 72, 4734-4738 (1975), Yusupova, G. Z., Yusupov, M. M., Cate, J. H. & Noller, H. F., *Cell* 106, 233-241 (2001)), and the spacing between these sequences (Chen, H., Bjerknes, M., Kumar, R. & Jay, E., *Nucleic Acids Res* 22, 4953-4957 (1994)). In certain cases mRNA structure (Gottesman, S. et al. in The Ribosome, Vol. LXVI (Cold Spring Harbor Laboratory Press, Cold Spring Harbor, N.Y.; 2001), Looman, A. C., Bodlaender, J., de Gruyter, M., Vogelaar, A. & van Knippenberg, P. H., *Nucleic Acids Res* 14, 5481-5497 (1986)), Liebhaber, S. A., Cash, F. & Eshleman, S. S., *J Mol Biol* 226, 609-621 (1992), or metabolite binding (Winkler, W., Nahvi, A. & Breaker, R. R., *Nature* 419, 952-956 (2002)), influences translation initiation, and in rare cases mRNAs can be translated without a SD sequence, though translation of these sequences is inefficient (Laursen, B. S., Sorensen, H. P., Mortensen, K. K. & Sperling-Petersen, H. U., *Microbiol Mol Biol Rev* 69, 101-123 (2005)), and operates through an alternate initiation pathway, Laursen, B. S., Sorensen, H. P., Mortensen, K. K. & Sperling-Petersen, H. U. Initiation of protein synthesis in bacteria. *Microbiol. Mol Biol Rev* 69, 101-123 (2005). For the vast majority of bacterial genes the SD region of the mRNA is a major determinant of translational efficiency. The classic SD sequence GGAGG (SEQ ID NO: 1) interacts through RNA-RNA base-pairing with a region at the 3' end of the 16S rRNA containing the sequence CCUCC (SEQ ID NO: 2), known as the Anti Shine Dalgarno (ASD). In *E. coli* there are an estimated 4,122 translational starts (Shultzaberger, R. K., Bucheimer, R. E., Rudd, K. E. & Schneider, T. D., *J Mol Biol* 313, 215-228 (2001)), and these differ in the spacing between the SD-like sequence and the AUG start codon, the degree of complementarity between the SD-like sequence and the ribosome, and the exact region of sequence at the 3' end of the 16S rRNA with which the mRNA interacts. The ribosome therefore drives translation from a more complex set of sequences than just the classic Shine Dalgarno (SD) sequence. For clarity, mRNA sequences believed to bind the 3' end of 16S rRNA are referred to as SD sequences and to the specific sequence GGAGG (SEQ ID NO: 1) is referred to as the classic SD sequence.

Mutations in the SD sequence often lead to rapid cell lysis and death (Lee, K., Holland-Staley, C. A. & Cunningham, P. R., *RNA* 2, 1270-1285 (1996), Wood, T. K. & Peretti, S. W., *Biotechnol. Bioeng* 38, 891-906 (1991)). Such mutant ribosomes mis-regulate cellular translation and are not orthogonal. The sensitivity of cell survival to mutations in the ASD region is underscored by the observation that even a single change in the ASD can lead to cell death through catastrophic and global mis-regulation of proteome synthesis (Jacob, W. F., Santer, M. & Dahlberg, A. E., *Proc Natl Acad Sci USA* 84, 4757-4761 (1987). Other mutations in the rRNA can lead to inadequacies in processing or assembly of functional ribosomes.

Methods are described herein, for example, for tailoring the molecular specificity of duplicated *E. coli* ribosome mRNA pairs with respect to the wild-type ribosome and mRNAs to produce multiple orthogonal ribosome orthogonal mRNA pairs. In these pairs the ribosome efficiently translates only the orthogonal mRNA and the orthogonal mRNA is not an efficient substrate for cellular ribosomes. Orthogonal ribosomes as described herein that do not translate endogenous mRNAs permit specific translation of desired cognate mRNAs without interfering with cellular gene expression. The network of interactions between these orthogonal pairs is predicted and measured, and it is shown herein that orthogonal ribosome mRNA pairs can be used to post-transcriptionally program the cell with Boolean logic.

Finding orthogonal ribosome orthogonal mRNA pairs requires the discovery of ribosome variants that specify the translation of the orthogonal mRNA with high efficiency. These ribosome variants must not interfere with ribosome assembly, rRNA processing or cellular viability, and must not significantly or detrimentally translate any of the thousands of endogenous transcripts. In addition it requires the discovery of an orthogonal mRNA that is robustly translated by only the orthogonal ribosome, but is not a substrate for the endogenous ribosome.

A selection approach for the discovery of orthogonal ribosome mRNA pairs can permit the interrogation of up to $10^9$ times more sequence space than has previously been considered by small screens or designed mutants. Described herein is a new tuneable positive and negative selection for evolution of orthogonal translational machinery. The selection methods are applied to evolving multiple orthogonal ribosome mRNA pairs (O-ribosome O-mRNA). Also described is the successful prediction of the network of interactions between cognate and non-cognate O-ribosomes and O-mRNAs. Knowledge of the specificity of these molecular interactions permits programming of post-transcriptional Boolean logic in cells.

Positive-Negative Selection Approach:

A selection approach for the identification of orthogonal ribosome orthogonal mRNA pairs, or other pairs of orthogonal molecules, entails a concerted use of positive and negative selection. In one aspect, for example, negative selection is used to remove from a library of mRNA sequences those members that are substrates for wild-type ribosomes, and positive selection is used to select from a library of mutated ribosomes those that efficiently translate the remaining mRNAs that are not translated by the wild-type ribosomes.

A number of different positive and negative selection agents can be used. Ideal positive and negative selections in, for example, *E. coli* would be tuneable in response to two small molecules (one for each selection) over a large dynamic range. Several positive selections have been used in *E. coli*, the most common of which involve conditional survival on antibiotics. Of these positive selections, the chloramphenicol acetyl-transferase gene in combination with the antibiotic chloramphenicol has proved one of the most useful. Others as known in the art, such as ampicillin, kanamycin, tetracycline or streptomycin resistance, among others, can also be used.

Negative selections in, for example, *E. coli* have used the ribonuclease barnase. However, barnase is both extremely toxic and constitutively active, which limits its utility in tuneable selections for the isolation of a range of activities. Perhaps the most widely used negative selection in, for example, gram negative bacteria uses the *Bacillus subtilis* sacB gene, which converts saccharose into levan sucrase and confers sucrose sensitivity on the cell. The selection, however, requires the forced uptake of sucrose by the addition of huge extracellular concentrations (5% or more). The stress of this procedure is believed to lead to mutations that bypass the stringency of the selection; while in principle the selection is tuneable, in practice such high concentrations of sucrose are required that the dynamic range is low (Galvao, T. C. & de Lorenzo, V., *Appl Environ Microbiol* 71, 883-892 (2005)). A novel, and likely tuneable negative selection involves uracil phosphoribosyltransferase (UPRT) (Galvao, T. C. & de Lorenzo, V., *Appl Environ Microbiol* 71, 883-892 (2005), Rasmussen, U. B., Mygind, B. & Nygaard, P., *Biochim Biophys Acta* 881, 268-275 (1986)). This enzyme operates in the nucleotide salvage pathway to convert uracil into uridine monophosphate, the source of all pyrimidine nucleoside triphosphates in the cell. If 5-fluorouracil is added to cells, it is converted to 5-fluoro-dUMP by UPRT which strongly inhibits thymidylate synthase (Neuhard, J. in Metabolism of Nucleotides, Nucleosides, and Nucleobases in Microorganisms. (ed. O. Munch-Petersen) 95-148 (Academic Press, New York, N.Y., New York; 1983)), and leads to cell death.

Figure 2A:
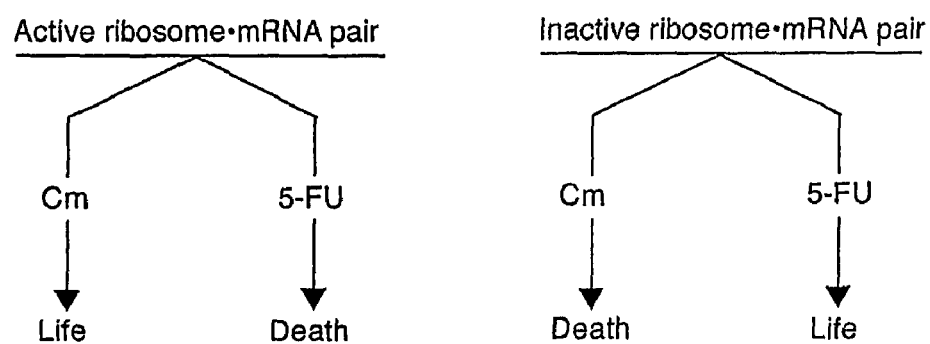

Selection of O-ribosome O-mRNA pairs is facilitated by a single transcript that can respond to either a positive or a negative selection depending on the identity and dose of a small molecule added to the media (FIG. 2a). One way to do this is to generate a single construct encoding a fusion polypeptide that comprises both the positive and negative selectable marker activities. The generation of fusion constructs is well known in the art. Positive and negative selectable markers as known in the art can be used in such a construct. As discussed above with respect to the markers themselves, the selectable markers will ideally each have a dynamic range that permits tuning the stringency of the selection to obtain a broader spectrum of selected mutant activity.

The dynamic range for selectable markers is preferably at least two fold, more preferably at least 5-fold, 10-fold, 50-fold, 100-fold, 500-fold or more. One of skill in the art can determine the dynamic range of a given selectable marker and its corresponding selection agent using, for example, an approach as described in the Examples herein. The decision of which selectable marker polypeptide to place N-terminal and which to place C-terminal in the construct can be empirical because there are only two choices for a given combination of two markers. However, where aspects of the structures and, for example, their sensitivities to alteration or steric hindrances, are known, those considerations can dictate which of the two orientations is most likely to work. Where necessary, short peptide linkers as known in the art can be used to space the two fused selectable markers apart sufficiently to preserve both selectable functionalities. Further, the Examples below describe methods useful to ascertain the function of both selectable marker polypeptides in the context of a fusion protein.

The methods described herein and exemplified in the Examples below permit the evolution of highly active and highly specific orthogonal ribosome mRNA pairs by gene duplication followed by a novel positive and negative selection. These pairs can be used, for example, to produce a transcript in a host cell that can only be translated by the cognate orthogonal ribosome, thereby permitting extremely sensitive control of the expression of a polypeptide encoded by the transcript. The pairs can thus be used to produce a polypeptide of interest by, for example, introducing nucleic acid encoding such a pair to a cell, where the orthogonal mRNA encodes the polypeptide of interest. The translation of the orthogonal mRNA by the orthogonal ribosome results in production of the polypeptide of interest. It is contemplated that polypeptides produced in cells encoding orthogonal mRNA•orthogonal ribosome pairs can include unnatural amino acids.

Unlike the progenitor ribosome in natural cells, orthogonal ribosomes are not responsible for synthesizing the proteome, and it will therefore be possible to further diverge their function. For example, it may be possible to produce ribosomes that decode extended codons (Magliery, T. J., Anderson, J. C. & Schultz, P. G., *J Mol Biol* 307, 755-769 (2001), Anderson, J. C., Magliery, T. J. & Schultz, P. G., *Chem Biol* 9, 237-244 (2002)), with greater efficiency and specificity, or specifically decode only a subset of natural codons. Each of these ribosomes would have applications for further expanding or altering the genetic code.

The methods described herein are applicable to the selection of orthogonal mRNA orthogonal rRNA pairs in species in which base pairing between ribosomal RNA and a ribosome binding sequence on mRNA occurs during the initiation of translation. Thus, the methods are broadly applicable across bacterial species, in which this mechanism is conserved. The sequence of 16S rRNA is known for a large number of bacterial species and has itself been used to generate phylogenetic trees defining the evolutionary relationships between the bacterial species (reviewed, for example, by Ludwig & Schleifer, 1994, FEMS Microbiol. Rev. 15: 155-73; see also Bergey's Manual of Systematic Bacteriology Volumes 1 and 2, Springer, George M. Garrity, ed.). The Ribosomal Database Project II (Cole J R, Chai B, Farris R J, Wang Q, Kulam S A, McGarrell D M, Garrity G M, Tiedje J M, *Nucleic Acids Res*, (2005) 33(Database Issue):D294-D296. doi: 10.1093/nar/gki038) provides, in release 9.28 (Jun. 17, 2005), 155,708 aligned and annotated 16S rRNA sequences, along with online analysis tools.

Phylogenetic trees, such as that shown in FIG. 6 are constructed using, for example, 16S rRNA sequences and the neighbor joining method in the ClustalW sequence alignment algorithm. Using a phylogenetic tree, one can approximate the likelihood that a given set of mutations (on 16S rRNA and corresponding translation control sequence on an mRNA) that render the set orthogonal with respect to each other in one species will have a similar effect in another species. Thus, the mutations rendering mRNA/16S rRNA pairs orthogonal with respect to each other in one member of, for example, the Enterobacteriaceae Family (e.g., *E. coli*) would be more likely to result in orthogonal mRNA/orthogonal ribosome pairs in another member of the same Family (e.g., *Salmonella*) than in a member of a different Family on the phylogenetic tree.

In some instances, where bacterial species are very closely related, it may be possible to introduce corresponding 16S rRNA and mRNA mutations that result in orthogonal molecules in one species into the closely related species to generate an orthogonal mRNA orthogonal rRNA pair in the related species. Also where bacterial species very are closely related (e.g., for *E. coli* and *Salmonella* species), it may be possible to introduce orthogonal 16S rRNA and orthogonal mRNA from one species directly to the closely related species to obtain a functional orthogonal mRNA orthogonal ribosome pair in the related species.

Alternatively, where the species in which one wishes to identify orthogonal mRNA orthogonal ribosome pairs is not closely related (e.g., where they are not in the same phylogenetic Family) to a species in which a set of pairs has already been selected, one can use positive-negative selection methods as described herein to generate orthogonal mRNA orthogonal ribosome pairs in the desired species. Briefly, one can prepare a library of mutated ribosome binding sequences linked to a sequence encoding a positive-negative selection fusion polypeptide as described herein (the bacterial species must be sensitive to the activity of the selection agents, a matter easily determined by one of skill in the art). The library can then be introduced to the chosen species, with selection against mRNAs that are substrates for wild-type ribosomes. A library of 16S rRNA sequences can be generated by mutating the 16S rRNA of the chosen species. The mutant 16S rRNA library can then be introduced to cells comprising the mRNAs that are not substrates for wild-type ribosomes, followed by positive selection for those cells expressing the positive selectable marker in order to identify orthogonal ribosomes that pair with the mRNAs selected in the first selection.

Ribosome binding sequences can and do differ in different species, although a region of complementarity to a region of corresponding 16S rRNA is maintained. Two approaches can be taken where there is not necessarily a known consensus ribosome binding sequence for a given species. In one approach, the sequences surrounding or adjacent to the translation start codon of a model transcript in that species, such as one for a housekeeping or other gene, can be used to generate the first library of mutated mRNA sequences—that is, the translation-regulatory sequences of a single transcript can be used to generate a mutated library of translation regulatory sequence linked to a positive-negative reporter as described herein. Negative and positive selection along with a library of mutant 16S rRNA sequences as described above will permit the isolation of orthogonal mRNA orthogonal ribosome pairs based on the members of the mutant translation regulatory sequence. In the other approach, mRNA sequences from the chosen species can be aligned with each other and with the region of 16S rRNA expected (based on similarities to *E. coli* 16S rRNA or other 16S rRNA for which the mRNA-interacting sequences are known) to base pair with the ribosome binding site using any of a number of different algorithms. The alignment permits the identification of conserved sequences most likely to interact with the 16S rRNA, thereby permitting the selection of a consensus for that species. An mRNA library diversified in that consensus region can then be generated to provide starting material for selection of orthogonal mRNA orthogonal ribosome pairs functional in that species as described herein.

The methods described herein are applicable to the identification of molecules useful to control translation or other processes in a wide range of bacteria, including bacteria of industrial and agricultural importance as well as pathogenic bacteria. Pathogenic bacteria are well known to those of skill in the art, and sequence information, including not only 16S rRNA sequence, but also numerous mRNA coding sequences, are available in public databases, such as GenBank. Common, but non-limiting examples include, e.g., *Salmonella* species, *Clostridium* species, e.g., *Clostridium botulinum* and *Clostridium perfringens*, *Staphylococcus* sp., e.g., *Staphylococcus aureus*; *Campylobacter* species, e.g., *Campylobacter jejuni*, *Yersinia* species, e.g., *Yersinia pestis*, *Yersinia enterocolitica* and *Yersinia pseudotuberculosis*, *Listeria* species, e.g., *Listeria monocytogenes*, *Vibrio* species, e.g., *Vibrio cholerae*, *Vibrio parahaemolyticus* and *Vibrio vulnificus*, *Bacillus cereus*, *Aeromonas* species, e.g., *Aeromonas hydrophila*, *Shigella* species, *Streptococcus* species, e.g., *Streptococcus pyogenes*, *Streptococcus faecalis*, *Streptococcus faecium*, *Streptococcus pneumoniae*, *Streptococcus durans*, and *Streptococcus avium*, *Mycobacterium tuberculosis*, *Klebsiella* species, *Enterobacter* species, *Proteus* species, *Citrobacter* species, *Aerobacter* species, *Providencia* species, *Neisseria* species, e.g., *Neisseria gonorrhea* and *Neisseria meningitidis*, *Heamophilus* species, e.g., *Haemophilus influenzae*, *Helicobacter* species, e.g., *Helicobacter pylori*, *Bordetella* species, e.g., *Bordetella pertussis*, *Serratia* species, and pathogenic species of *E. coli*, e.g., Enterotoxigenic *E. coli* (ETEC), enteropathogenic *E. coli* (EPEC) and enterohemorrhagic *E. coli* O157:H7 (EHEC).

Bacterial Transformation:

The methods described herein rely upon the introduction of foreign or exogenous nucleic acids into bacteria. Methods for bacterial transformation with exogenous nucleic acid, and particularly for rendering cells competent to take up exogenous nucleic acid, is well known in the art. For example, Gram negative bacteria such as *E. coli* are rendered transformation competent by treatment with multivalent cationic agents such as calcium chloride or rubidium chloride. Gram positive bacteria can be incubated with degradative enzymes to remove the peptidoglycan layer and thus form protoplasts. When the protoplasts are incubated with DNA and polyethylene glycol, one obtains cell fusion and concomitant DNA uptake. In both of these examples, if the DNA is linear, it tends to be sensitive to nucleases so that transformation is most efficient when it involves the use of covalently closed circular DNA. Alternatively, nuclease-deficient cells (RecBC$^-$ strains) can be used to improve transformation.

Electroporation is also well known for the introduction of nucleic acid to bacterial cells. Methods are well known, for example, for electroporation of Gram negative bacteria such as *E. coli*, but are also well known for the electroporation of Gram positive bacteria, such as *Enterococcus faecalis*, among others, as described, e.g., by Dunny et al., 1991, Appl. Environ. Microbiol. 57: 1194-1201.

The positive-negative selection approach described herein for the selection of orthogonal ribosome orthogonal mRNA pairs can be applied to the selection of additional pairs of orthogonal molecules. For example, orthogonal promoter/polymerase pairs can be identified by application of the positive-negative selection approach described herein. By analogy to the methods described herein for selection of orthogonal ribosome orthogonal mRNA pairs, one can generate a library of promoters and screen using negative selection (e.g., 5-FU/UPRT selection) for promoters that are not transcribed by endogenous polymerases, or, for that matter, a desired exogenous polymerase expressed in that cell. One can then transform the negative-selected cells with a library encoding mutant polymerase and subject the cells to positive selection for those that express the positive selectable marker (e.g., CAT) from a mutant promoter selected in the first step. The result is a mutant promoter that is not recognized by wild-type polymerases and a polymerase that specifically recognizes that mutant promoter. Together they constitute a very specific means of gene regulation.

A similar approach can be taken to the selection of, for example, riboswitches or riboregulators. A "riboswitch" is an mRNA structure that can fold in the presence of a metabolite or other small molecule or ion to regulate translation by altering mRNA conformation. Thus, riboswitches are structured domains in the non-coding portions of some mRNAs that sense the presence of a metabolite. Metabolite binding causes allosteric changes in the mRNA that result in changes in processes such as translation initiation or translation termination. Riboswitches are further described in Mandal & Breaker, 2004, Nat. Rev. Mol. Cell. Biol. 5:451-63. Using a positive-negative selection approach as described herein, one can, for example, select from an mRNA library those sequences able to bind small molecules and up- or down-regulate gene expression. This can be accomplished, for example, by placing a library of mRNA sequences 5' of the SD sequence and identifying those sequences that inactivate translation for the SD sequence (5-FU/UPRT selection). The small molecule is then added, with selection for re-activation of translation by positive selection. A reciprocal approach can be taken to provide small molecule repressors of gene expression.

A "riboregulator" is a small RNA that regulates gene expression. "Riboregulators" are described in, for example, Eddy, 1999, Curr. Opin. Genet. Dev. 1999 9:695-9 and Lease et al., 1998, Proc. Natl. Acad. Sci U.S.A. 95:12456-61. By replacing the small molecule in the riboswitch example above with the expression of a small non-coding RNA, one can identify riboregulator RNAs that activate or repress mRNA translation.

Positive-negative selection can also be used to identify modified transcription factor/transcription factor binding site pairs. In this approach, a known transcription factor binding site can be altered, in the most extreme cases to completely random sequence. Sequences that do not lead to transcription with the wild-type factor are selected by negative selection with 5-FU/UPRT. A library of mutant transcription factors is then introduced, with positive selection for the activation of transcription from the active site that leads to expression of the positive selectable marker, e.g., CAT.

EXAMPLES

Example 1

Generation and Testing of a Positive-Negative Selectable Marker Fusion Construct A genetic fusion was generated between the chloramphenicol acetyl-transferase (cat) gene and the uracil phosphoribosyltransferase (upp) gene, downstream of a constitutive promoter and wild type ribosome-binding site, on a p15A derived vector (maintained at 10-15 copies per cell). Both CAT and UPRT function as trimers, but whereas the CAT trimer has been crystallized (Leslie, A. G., *J Mol Biol* 213, 167-186 (1990)), the UPRT trimer has an unknown structure and symmetry (Rasmussen, U. B., Mygind, B. & Nygaard, P., *Biochim Biophys Acta* 881, 268-275 (1986)). The correct linkage to produce both activities in a single polypeptide was therefore unknown. However, it has previously been observed that CAT is sensitive to fusions to its N terminus, and on this basis it was decided to create a cat-upp fusion.

Figure 2B:
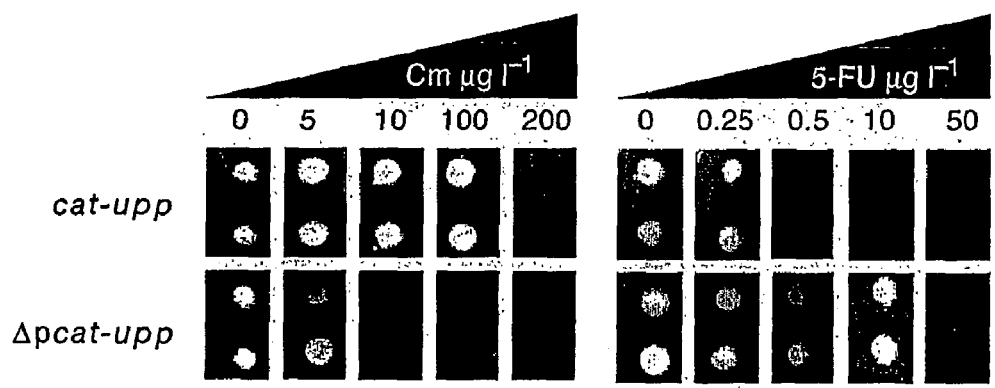

P21, a vector expressing a CAT-UPRT fusion, has a p 15A origin of replication, a cat-upp fusion downstream of a constitutive version of the Trp promoter, and a tetracycline resistance marker. All Bsa I restriction sites have been removed to allow enzymatic inverse PCR mutagenesis (Yusupova, G. Z., Yusupov, M. M., Cate, J. H. & Noller, H. F., *Cell* 106, 233-241 (2001)) or library construction with the vector as a template. The plasmid was created in several steps using standard molecular biology methods (plasmid map available below). Enzymatic inverse PCR (as described in detail for library construction) was used to construct P23, the promoterless cat-upp fusion, and P24, a start codon deleted cat-upp fusion using p21 as a template. The complete sequence of the oligonucleotides used to construct these vectors can be found below.

deletion of genomic upp, the cat-upp fusion allowed cells to survive on chloramphenicol concentrations of 150 µg ml$^{-1}$, while Δpcat-upp only led to chloramphenicol resistance at concentrations between 5 µg ml$^{-1}$ and 10 µg ml$^{-1}$ (FIG. 2*b*). These experiments demonstrate that CAT is produced in a functional form from the cat-upp fusion and the dynamic range of this positive selection is 15-fold.

To ascertain if UPRT was active in the cat-upp fusion and to assess the dynamic range of the 5-FU mediated negative selection the survival of cells containing cat-upp/GH371 and Δpcat-upp/GH371 was measured on increasing concentrations of 5-FU. Cat-upp/GH371 died on 5-FU concentrations of 0.5 µg ml$^{-1}$ while Δpcat-upp/GH371 survived on 5-FU up to 20 µg ml$^{-1}$. These experiments demonstrate that UPRT is produced in a functional form from the cat-upp fusion and the dynamic range of this negative selection is 50-fold (FIG. 2*b*). The survival spectrum of Δpcat-upp/GH371 on Chloramphenicol or 5FU was indistinguishable from the survival of Δ/GH371 (Δ is a plasmid in which the entire cat-upp ORF is deleted) demonstrating that there is no measurable read through of the cat-upp ORF derived from leaky transcription of other plasmid encoded genes.

Model enrichment studies were performed to examine the potential of the system for selecting orthogonal SD sequences that are not substrates for the endogenous ribosome, and for selecting complementary ribosomes. These model selections are summarized in Table 1, below.

TABLE 1

Model Selections

| A. Model Selections for functional ribosome mRNA pair | | | | | | | | | | | | |
|---|---|---|---|---|---|---|---|---|---|---|---|---|
| Starting Ratio[a] | 1:50 | | 1:500 | | 1:5 × 10$^3$ | | 1:5 × 10$^4$ | | 1:5 × 10$^5$ | | 1:5 × 10$^6$ | |
| Cell dilution | 10$^{-4}$ | 10$^{-5}$ | 10$^{-3}$ | 10$^{-4}$ | 10$^{-2}$ | 10$^{-3}$ | 10$^{-1}$ | 10$^{-2}$ | neat | 10$^{-1}$ | neat | 10$^{-1}$ |
| Cm$^{Rb}$ (+P$^c$) | 199 | 28 | 226 | 25 | 191 | 18 | 229 | 21 | 148 | 27 | 20 | 2 |
| | (100) | | (100) | | (100) | | (100) | | (100) | | (100) | |
| Enrichment Factor | >50 | | >500 | | >5 × 10$^3$ | | >5 × 10$^4$ | | >5 × 10$^5$ | | >5 × 10$^6$ | |

| B. Model Selections for non-functional ribosome mRNA pair | | | | | | | | |
|---|---|---|---|---|---|---|---|---|
| Starting Ratio[a] | 1:10 | | 1:100 | | 1:10$^3$ | | 1:10$^4$ | |
| Cell Dilution | 10$^{-4}$ | 10$^{-5}$ | 10$^{-3}$ | 10$^{-4}$ | 10$^{-2}$ | 10$^{-1}$ | 10$^{-2}$ | 10$^{-1}$ |
| Not 5FU$^{Sd}$ (ΔP$^e$) | 51 | 2 | 62 | 9 | 53 | 8 | 10 | 1 |
| | | (100) | | (100) | | (100) | | (100) |
| Enrichment factor | >10 | | >100 | | >1 × 10$^3$ | | >1 × 10$^4$ | |

[a]Calculated from colony forming units (c.f.u.) of the ΔPromoter and + Promoter clones on media containing 25 µg ml$^{-1}$, tetracycline, without chloramphenicol or 5-FU, prior to mixing.
[b]Approximately 10$^8$ c.f.u. were plated.
[c]The percentage of these clones with a promoter (10 characterized by colony PCR and sequencing).
[d]Approximately 10$^6$ c.f.u. were plated.
[e]The percentage of these clones without a promoter (10 characterized by colony PCR and sequencing).

To establish that both CAT and UPRT were functionally expressed from the cat-upp fusion, and to measure the dynamic range of each selection, two constructs were created. One construct constitutively expresses the cat-upp fusion, and is a maximum translation control, and the other construct Δpcat-upp has the entire promoter of the cat-upp fusion deleted and is a minimum translation control. When transformed into a strain of *E. coli* (GH371), containing an ORF In the first selection the enrichment of an inactive ribosome mRNA pair from a vast excess of active ribosome mRNA pairs was modeled. Δpcat-upp/GH371 were mixed with a 10 to 10$^4$ fold excess of cat-upp/GH371 and the mixture selected on 0.5 µg ml$^{-1}$ 5-FU. The ratio of cells surviving to the total number of cells plated correlates well with the ratio of Δpcat-upp to cat-upp without selection. Colony PCR confirmed that 100% of the selected clones were Δpcat-upp. These experiments demonstrate that the UPRT based negative selection allows the enrichment of clones that are not substrates for the endogenous ribosome from a greater than $10^4$ fold excess of mRNA sequences that are substrates for the endogenous ribosome.

In a second selection the enrichment of active ribosome mRNA pairs from a vast excess of inactive ribosome mRNA pairs was modeled (Table 1). cat-upp/GH371 were mixed with a 10- to 106 fold excess of cells containing Δpcat-upp/GH371. The ratio of cells surviving on 100 µg ml$^{-1}$ chloramphenicol to the total number of cells plated correlates well with the ratio of cat-upp/GH371 to Δpcat-upp/GH371 without selection, and colony PCR confirmed that the selected clones were cat-upp. These experiments demonstrate that the CAT based positive selection can enrich active ribosome mRNA pairs from greater than $10^5$ fold excess of non-functional pairs.

Example 2

Design and Construction of SD•ASD Libraries

Figures 3A, 3B:
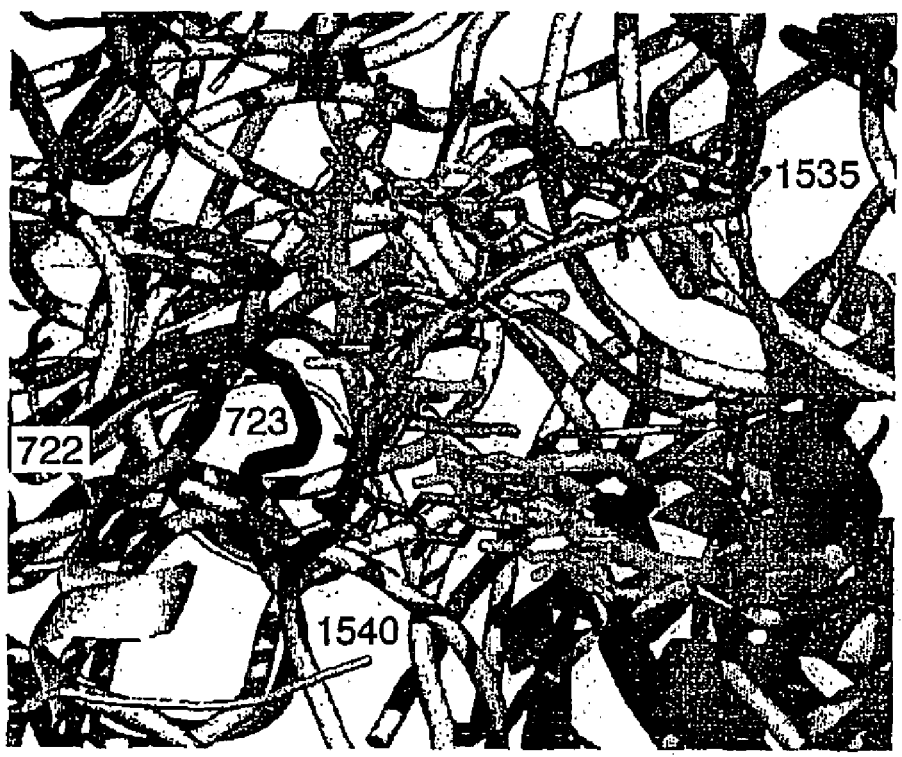

A) mRNA Library:

Analysis of the genome-wide variation in sequence 5' to AUG initiation codons has demonstrated that the highest information content for ribosome binding is between −7 and −13, with the information that specifies ribosome binding partitioned across this sequence differently for different sequences in the genome (Shultzaberger, R. K., Bucheimer, R. E., Rudd, K. E. & Schneider, T. D., *J Mol Biol* 313, 215-228 (2001)). A library was designed that mutates all seven nucleotides from −7 to −13 to all possible sequence combinations (FIG. 3a). This library contains all potential five base SD sequences, including those sequences that contain wild-type bases, giving a theoretical diversity of $4^7=16,384$. In addition it allows the region of base pairing with the ribosome to vary in register with respect to the start codon.

The mRNAlib was created by enzymatic inverse PCR using the primers

```
                                                    (SEQ ID NO: 3)
5'-GGGAAAGGTCTCCCGCTTTCANNNNNNNNCCGCAAATGGAGAAAAAA

TCACTGGATATACC-3'
and (SEQ ID NO: 4)
5'-GGAGTAGGTCTCAAGCGGCCGCTTCCACACATTAAACTAGTTC-3'
``` and p21 as template. Reactions contained: 20 pmol forward primer, 20 pmol reverse primer, 10 ng template plasmid, 40 pmol dNTPs, 1× Expand buffer 2 (Roche), in a total volume of 49.5 µl. 1.75 U Expand High Fidelity DNA polymerase (Roche, 3.5 U µl$^{-1}$) was added to the reaction at 80° C. Reactions were cycled in touchdown PCR (94° C., 20 s; 65° C., 20 s (−1° C. cycle$^{-1}$); 68° C., 8 min) for 20 cycles, followed by amplification (94° C., 20 s; 50° C., 20 s; 68° C., 8 min) for 20 cycles. The resulting PCR product (5 µg) was purified (Qiagen PCR purification), digested (Dpn I (40 U, 6 h); Bsa I (50 U, 6 h), re-purified (Qiagen PCR purification), ligated (T4 DNA ligase (16° C., 12 h), ethanol precipitated, and transformed by electroporation into DH10B electrocompetent cells. Plasmid DNA was isolated and retransformed into GH371 cells for selections. This strain (a generous gift from J. Christopher Anderson, UCSF) is a derivative of Gene-Hogs *E. coli* in which the upp ORF is completely deleted. Similar strains having the non-functional upp ORF can be generated in a straightforward manner using gene knockout methods well known in the art. Alternatively, upp mutants can be selected as necessary, for example, by exposing *E. coli* strains to low doses of 5-FU and selecting for surviving cells that spontaneously down-regulate the upp gene.

The mRNAlib library realizes greater than $10^7$ independent transformants, providing greater than 99.99% confidence, as determined from a Poisson distribution (Ladner, R. C. in Phage Display of Peptides and Proteins. (eds. B. K. Kay, J. Winter & J. McCafferty) 151-194 (Academic Press, San Diego; 1996)), that the library is complete. To determine the fraction of mRNAlib clones that are substrates for the endogenous ribosome GH371 cells transformed with mRNAlib were plated on agar plates containing no chloramphenicol, and on agar plates containing chloramphenicol at a concentration just sufficient to kill untransformed cells (10 µg/ml$^{-1}$). 50% of cells survive on 10 µg ml$^{-1}$, suggesting that approximately half the library is translated to some extent by endogenous ribosomes. Since the theoretical diversity of the library is 16,384, and sequencing reveals no significant bias in its nucleotide composition, approximately 8,000 distinct sequences are not translated by the endogenous ribosome and are potentially orthogonal.

B) rRNA Library:

To create the ribosomal RNA library (rRNAlib) eight nucleotides in the 16S rRNA (FIGS. 3a,b) were mutated. Six of these nucleotides are in the region from 1536-1541 at the 3' end of the 16S rRNA. Five of these bases pair with the mRNA in the classic SD ASD (Yusupova, G. Z., Yusupov, M. M., Cate, J. H. & Noller, H. F., *Cell* 106, 233-241 (2001)), interaction and are clearly important determinants of translational efficiency on endogenous mRNAs, whereas the sixth allows additional flexibility in the spacing between the SD and the ribosomal A site. The final two mutated bases, 722 and 723, form a bulge proximal to the minor groove of the SD helix formed between the ribosome and mRNA (Yusupova, G. Z., et al., Supra). 722 forms a non-canonical G-G base pair with nucleotide 767. 723 is unpaired and comes close to the minor groove of the SD helix, but in the 5 Å structure showing the path of the mRNA through the ribosome (Yusupova, G. Z., et al., Supra), the molecular details of any interaction between the 723 bulge and the SD helix are undefined. These mutations acknowledge the possibility that the 723 bulge might monitor the geometry of the minor groove of the SD helix, and explore the possibility that mutations at these positions might allow access to an expanded set of functional SD ASD sequences.

The plasmids for rRNA library construction are derivatives of pSP72 and pSP73 (Promega), from which Bsa I and Pst I sites were removed, and new Pst I and NgoM IV sites engineered in the β-lactamase gene. The *E. coli* rrnB 23S-containing fragment was subcloned into the pSP73 derivative as an Xba I, BamH I fragment from pSTL102 (A generous gift from Professor Harry Noller, University of California, Santa Cruz) yielding the plasmid pJC23S. The *E. coli* rrnB 16S fragment was amplified from pSTL102 with Cla I and Xba I flanking sequence and cloned into the pSP72 derivative using Cla I and Xba I, yielding pJC16S. Plasmid maps of pJC23S and pJC16S are available below. For expression of mutant rRNA sequences, a derivative of pTrcHis2 A (Invitrogen) was constructed, designated pTrcΔKan. A plasmid map of pTrcΔ-Kan can be found below.

The rRNAlib library of 16S rRNA mutants was generated by two rounds of enzymatic inverse PCR each followed by Dpn I, Bsa I digestion, ligation and transformation, as described for the construction of mRNAlib. This was followed by operon assembly with the 23S/5S fragment from pJC23S and transfer of the complete operon to a promoter. To construct the library at the 3' end of the 16S rRNA, pJC16S was used as a template with oligonucleotides 5'-GGAAAG-GTCTCAGGTTGGATCANNNNNNTACCT-TAAAGAAGCGTACTTTGTAG-3' (SEQ ID NO: 5) and 5'-GAGTAGGTCTCAAACCGCAGGTTCCCCTACG-3' (SEQ ID NO: 6). The resulting library was used as a template for the randomization of the nucleotides at positions 722 and 723 using the oligonucleotides 5'-GGAAAGGTCTCA-GAATACCGNNGGCGAAGGCGGCCCCCTGGACGAA-3' (SEQ ID NO: 7) and 5'-GAGTAGGTCTCAATTCCTC-CAGATCTCTACGCATTTCAC-3' (SEQ ID NO: 8). 16S rRNA mutant libraries in the pJC16S backbone were assembled with the 23S and 5S rRNA containing fragment in pJC23S by Pst I, Xba I subcloning of gel purified DNA fragments. The resulting pJC16S23S plasmid contains the library of rrnB rRNA operons. These were transferred to the pTrcΔ expression plasmid by BamH I, Nde I and Xho I digestion of pJC16S23S, and BamH I, Stu I, and Xho I digestion of pTrcΔKan. The resulting BamH I, Xho I fragments were gel purified and subcloned to create rRNAlib.

The library makes no assumptions about the nucleotide composition of the eight mutated nucleotides and allows all four bases at each of the eight positions giving a theoretical diversity of $4^8$=65,536. Greater than $10^7$ independent transformants of rRNAlib were realized providing greater than 99.99% confidence that the library is complete as calculated by Poisson sampling, (Ladner, R. C., Supra). The unique pairs of mRNAlib and rRNAlib library members form a matrix of greater than $10^9$ combinations.

Example 3

Selection and Characterization of Orthogonal Ribosome mRNA Pairs

To interrogate the matrix for O-ribosome O-mRNA combinations a two-step approach was taken. In the first step mRNA sequences that are not translated by endogenous ribosomes were screened for. To remove mRNAlib members that are substrates for endogenous ribosomes, a negative selection was performed by growing the ribosome binding site library in the presence of 5-FU. Active ribosome binding sites direct the synthesis of the cat-upp fusion, and UPRT protein converts 5FU to a toxic product, poisoning the cell. In contrast ribosome-binding sites that are not substrates for the endogenous ribosome do not direct the synthesis of UPRT and survive the selection. The library is therefore selectively enriched in O-mRNAs. Ten clones from this first selection were sequenced at random. Ten distinct sequences were observed at this point, suggesting the library is still quite diverse, as expected from the previous observation that half of the mRNAlib library is not a substrate for the endogenous ribosome prior to 5FU selection.

In a second step, ribosomes were screened for that translate the selected orthogonal mRNAs. Cells containing the selected ribosome binding sites were transformed with the library of mutant ribosomes, yielding $10^{11}$ transformants, over-sampling the total theoretical diversity of ribosome mRNA combinations by two orders of magnitude. The library was grown in the presence of chloramphenicol, and active ribosome O-mRNA pairs selected. In this selection only for pairs with comparable activity to the wild-type pair were sought. Under less stringent conditions it may be possible to isolate less highly active, but still active ribosome mRNA pairs.

The methods used for the selections are detailed briefly below. GH371 E. coli were transformed with mRNAlib, then recovered for 1 h in SOC. The library was then plated on selective media (M9 agar containing 0.4% glucose, 0.2% casaminoacids, 25 µg ml$^{-1}$ tetracycline, 0.5 µg ml$^{-1}$ 5-FU). After 24 h, surviving cells were pooled and used to prepare electrocompetent GH371/mRNAlib(−)cells.

GH371/mRNAlib(−) cells were transformed with the rRNAlib library, and recovered for 1 h in SOB containing 2% glucose. The recovered cells were used to inoculate 200 ml of LB-GAT (LB media supplemented with 2% v/v glucose, 100 µg ml$^{-1}$ ampicillin, 25 µg ml$^{-1}$ tetracycline), grown to saturation, and pelleted by centrifugation at 3000 g. The cells were resuspended in LB-AT ((LB media supplemented with 100 µg ml$^{-1}$ ampicillin, 25 µg ml$^{-1}$ tetracycline) and incubated (37° C., 300 rpm, 1 h) before pelleting at 3000 g. Cells were resuspended in an equal volume of LB-ATI (LB medium containing 25 µg ml$^{-1}$ ampicillin and 7.5 µg ml$^{-1}$ tetracycline, 1 mM isopropyl-D-thiogalactopyranoside (IPTG)) and incubated (37° C., 300 rpm, 3.5 h). 1 ml aliquots (OD$_{600}$=1) were plated on LB ATI agar supplemented with 100 µg ml$^{-1}$ chloramphenicol and incubated (16 h, 37° C.).

Total plasmid DNA was isolated from selected clones. To purify rRNAlib members from their cognate mRNAlib members and vice versa a fraction of each plasmid sample was digested with restriction enzymes that recognize sites found only in rRNAlib (Bsa I) or in the mRNAlib (Not I) and the digests re-transformed into GH371. Individual transformants were replica plated on ampicillin and tetracycline to confirm the separation. Plasmid DNA was isolated and sequenced by standard methods.

Competent GH371/mRNAlib clones were transformed in parallel with either pTrc-WT (encoding rRNA from the rrnB operon) or the corresponding rRNAlib member. Cells were recovered in SOB with 2% glucose and transferred to LB GAT and grown overnight at 200 rpm. Cells (100 µl) were transferred to each well of a 96 well culture block and pelleted by centrifugation at 3000 g. Cells were resuspended in 1 ml LB AT, incubated (37° C., 300 rpm, 1 h) and then pelleted at 3000 g. They were resuspended in an equal volume of LB ATI and incubated (37° C., 300 rpm, 3.5 h), before being arrayed using a 96 well pin tool on LB ATI agar containing chloramphenicol at concentrations from 0 to 100 µg ml$^{-1}$. To measure the interactions that form the ribosome mRNA network between the three orthogonal ribosomes and mRNAs, assays were repeated with cognate and non-cognate ribosome mRNA pairs.

From the two-step selection, 51 individual ribosomal RNAs and the corresponding O-mRNAs were sequenced (FIG. 4a). Four distinct O-mRNAs were discovered (FIG. 4a), with two of the four isolated sequences containing non-programmed deletions in the mutagenized region. Since sequencing of ten clones after the negative selection returned 10 distinct sequences, and the diversity was estimated at that stage to be approximately 8,000, it is concluded that the positive selection led to a significant (~2,000-fold) convergence in the mRNA sequences. These results highlight the advantages of selection methods for finding O-ribosome O-mRNA pairs. While it may be relatively simple to find mRNA SD sequences that do not function with the endogenous ribosome (for example by altering the mRNA sequence to remove base pairing with the 16S rRNA) there are no highly active, non-toxic ribosomes to complement the vast majority of these mRNA sequences and the chance of picking a mRNA sequence that can be complemented is very low.

Ten distinct ribosomes with complementarity to the O-mRNAs were discovered (FIG. 4a). The mutations in the 16S rRNA of the selected ribosomes are highly convergent at several positions. At position 1536, U (59%) dominates. At position 1537, G is very strongly selected (90%). Position 1539 contains solely purines: A (69%) or G (31%), and position 1540 is dominated by G (73%). The wild type residues are selected with a reasonable frequency at some positions: 1535C is recovered in 13% of sequences, and 1538C in 51% of sequences. The sequence conservation at positions 722 and 723 in the selected clones is low. However, purines and pyrimidines are mutually exclusive at these positions in a given selected sequence, and this may reflect a selection constraint that conserved the volume occupied by this loop.

Ten pairs of cognate ribosome mRNA sequences were identified in this initial screen (FIG. 4b). Each mRNA has an $IC_{50}$ of 10 μg ml$^{-1}$ or less on chloramphenicol in the absence of its cognate ribosome, and is therefore orthogonal (O-mRNA) with respect to the endogenous ribosome. Addition of the co-selected ribosome increases the $IC_{50}$ to greater than or equal to 150 μg ml$^{-1}$ in all cases. The co-selected ribosomes are therefore highly active, and translate the message from the O-mRNA as well or better than the endogenous ribosome translates the same message from a classic SD sequence. The ten pairs fall into three classes on the basis of predicted SD ASD base pairing, with each class forming a SD ASD interaction over exactly 5 base pairs. The first class of pairs contains the bases ACCAC −6 (SEQ ID NO: 9; numbering refers to position of 3' base) to AUG in the mRNA. This is complemented by four distinct ribosomes that can Watson-Crick pair with the mRNA over five bases. Two distinct registers of the 16S rRNA with respect to the SD sequence are observed. In the first register, exemplified by rRNA-1, bases 1536 to 1540 of the 16S rRNA Watson-Crick pair with mRNA-A. In the second register, exemplified by pairs A2, A3, and A4, bases 1537 to 1541 of the 16S rRNA Watson-Crick pair with the cognate mRNAs. Pyrimidines are favored in the selected sequences at the two positions immediately 5' to the region of the rRNA that Watson-Crick base pairs with the mRNA. A second class of pairs (B5, B6, B7, B8) contain the sequence ACUGC −7 (SEQ ID NO: 10) to AUG in the O-mRNA. The region 1537 to 1541 of 16S rRNA Watson-Crick base pairs with this O-mRNA sequence. Positions 1535 and 1536 in these clones are dominated by pyrimidines. A third class of pairs (C9, D10) contains the sequence AUCCC −6 (SEQ ID NO: 11) to AUG in the O-mRNA. The region 1536 to 1540 of the 16S rRNA Watson-Crick base pairs with the O-mRNA.

Figure 4C:
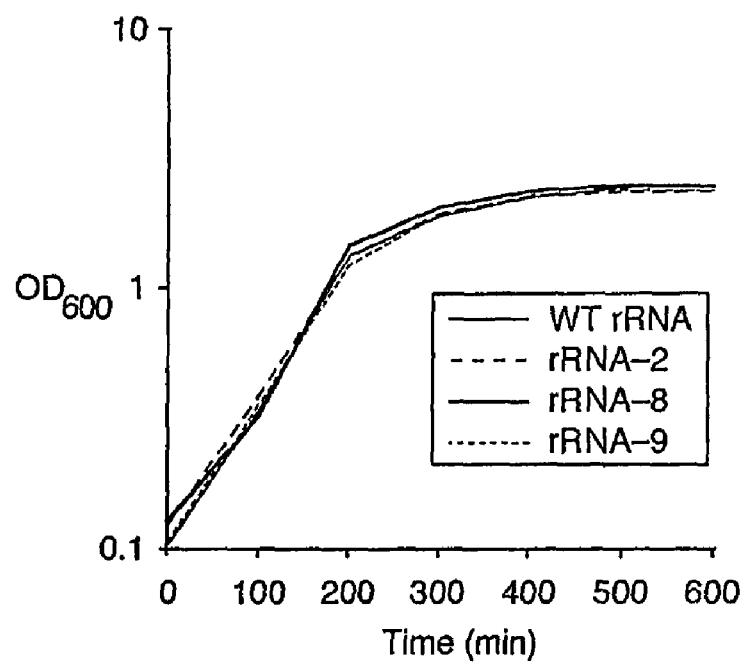

The selected rRNA sequences have between 5 and 8 mutations with respect to the wild-type rRNA sequence, making it likely that they will discriminate against the translation of endogenous transcripts. Moreover, since cells have been grown for many generations in the presence of the mutant ribosomes, it is likely that the selected mutant ribosomes do not mis-regulate proteome synthesis. Indeed, negative selection against proteome mis-regulation may be responsible for the strong convergence of residues 1535 and 1536 which lie outside the Watson-Crick paired region of the selected ribosome mRNA interactions, but form key G-C base pairs in the classic SD ASD helix. To demonstrate that the mutant ribosomes do not detrimentally mis-regulate the translation of transcripts that affect cell viability ribosome synthesis was induced and cell growth was monitored over ten hours (FIG. 4c). In contrast to designed "specialized ribosomes" that lyse cells after 3 hours (Hui, A. & de Boer, H. A., Supra), Lee, K. et al., Supra, Wood, T. K. & Peretti, S. W., *Biotechnol. Bioeng* 38, 891-906 (1991)), the selected ribosomes, do not lyse cells, and cells transformed with these ribosomes double at the same rate as cells containing wild-type ribosomes. Moreover, several of the selected rRNA sequences have been transferred to the constitutive and strong P1P2 promoter (from which wild-type rRNA is synthesized) without significantly affecting cell growth.

Figure 4D:
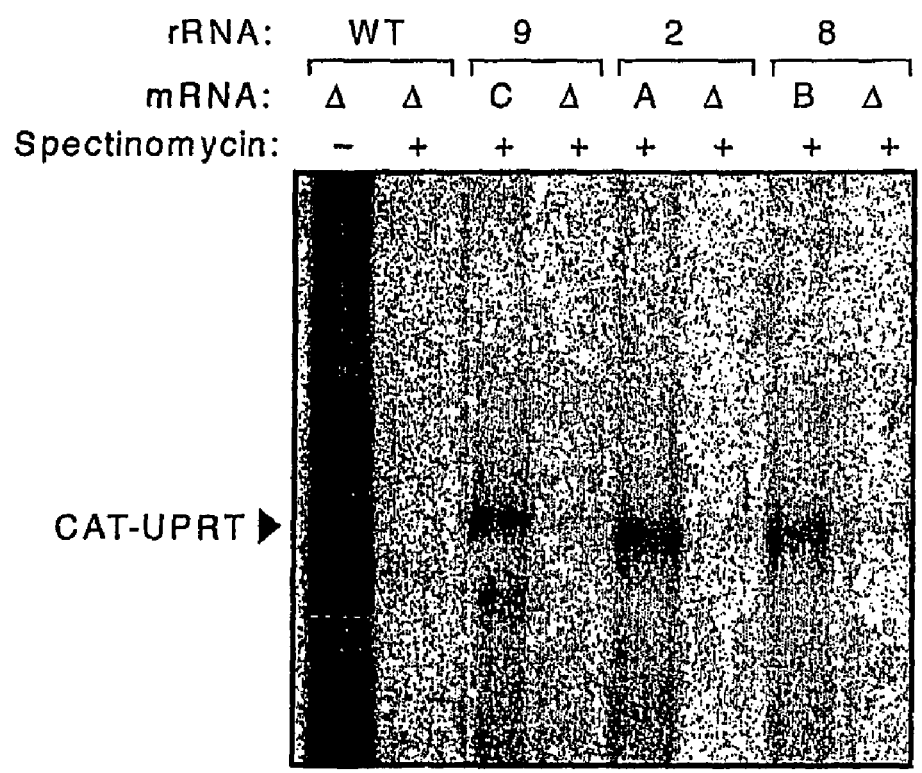

To globally assess the extent of mutant ribosome orthogonality with respect to all cellular transcripts, cellular ribosomes were inactivated using spectinomycin and translation was measured from mutant ribosomes, which are spectinomycin-resistant by virtue of a C1192U mutation in 16S rRNA (Sigmund, C. D., Ettayebi, M. & Morgan, E. A., *Nucleic Acids Res* 12, 4653-4663 (1984)), (FIG. 4d). The methods used are described briefly as follows. GH371/rRNAlib/mR-NAlib clones were grown to saturation in LB GAT. The cells were pelleted by centrifugation at 3000 g and resuspended at $OD_{600}$=0.1 in M9 minimal media supplemented with 2% glycerol, all nineteen natural amino acids except methionine, 25 μg ml$^{-1}$ ampicillin, 7.5 μg ml$^{-1}$ tetracycline. Cells were incubated (37° C., 300 rpm, 1 h), and then pelleted before resuspension in an equal volume of identical medium, with the addition of 1 mM IPTG. After incubation (37° C., 300 rpm, 1 h), spectinomycin (500 μg ml$^{-1}$) was added to the media to inhibit endogenous protein synthesis. After a further 10 minutes (Rasmussen, et al., Supra). $^{35}$S methionine (>1000 Ci mmol$^{-1}$, Amersham) was added to a final concentration of 30 nM. Cells were grown for a further 3 hours, and harvested by centrifugation. Cells (diluted to $OD_{600}$=0.1) were lysed by boiling in SDS loading buffer. The resulting lysate was chilled on ice and then separated by 4-12% SDS-PAGE (200V, 35 min). The gel was dried and imaged on a Storm 840 Phosphoimager (Amersham). To measure the effects of orthogonal pairs on the growth of cells, GH371 were grown in LB AT, pelleted at 3000 g, diluted to OD 600=0.1 in LB ATI and incubated (37° C., 300 rpm, 10 h) until saturation. $OD_{600}$ measurements were taken every 100 minutes.

In the absence of their cognate ribosome-binding site, mutant ribosomes do not synthesize endogenous protein. However, in the presence of the cat-upp fusion downstream of a cognate ribosome binding site greater than 90% of spectinomycin-resistant translation is involved in CAT-UPRT synthesis. Control experiments with cat-upp on a wild type SD sequence show that the protein is expressed at levels below many endogenous proteins (not shown), demonstrating that this result does not come from overexpression of the cat-upp fusion. The pairs described here are therefore orthogonal ribosome mRNA pairs (O-ribosome O-mRNA pairs).

Example 4

Boolean Logic with Orthogonal Ribosomes

To demonstrate the potential of orthogonal ribosome mRNA pairs for the programmable synthesis of Boolean logic, simple logic gates were designed for which the output is controlled by an orthogonal ribosome. The components of the circuit are an O-ribosome, a gene encoding the α-fragment of β-galactosidase on the corresponding orthogonal SD sequence (Ullmann, A., Jacob, F. & Monod, J., *J Mol Biol* 24, 339-343 (1967)), and a gene encoding the ω-fragment of α-galactosidase on a wild-type SD sequence (Ullmann, et al., Supra). Constructs and methods used are detailed briefly as follows. A plasmid expressing β-galactosidase α-fragment was constructed by replacing the cat-upp fusion gene in p21 with a PCR fragment of the *E. coli* lacZ gene downstream of an mRNA-C or mRNA-A SD sequence. rRNA-9 or rRNA-2 was transformed with or without a p21-derivative, containing the α complementing fragment of lacZ downstream of the cognate RBS, into DH10B or BW26444 cells (a generous gift of B. L. Wanner, Purdue University, West Lafayette). DH10B cells produce the a) fragment of β-galactosidase due to a chromosomal deletion within lacZ corresponding to amino acids 11-41. lacZ is completely deleted from BW26444 (Δ(araD-araB)567, Δ(lacA-lacZ)519(::FRT), lacIp-4000(lacI$^Q$), λ$^-$, rpoS396(Am), rph-1, Δ(rhaD-rhaB)568, hsdR514). Cells were recovered in SOB with 2% glucose and transferred to LB GAT and grown overnight at 200 rpm. Cells (100 μl) were transferred to each well of a 96 well culture block and pelleted by centrifugation at 3000 g. Cells were resuspended in 1 ml LB AT, incubated (37° C., 300 rpm, 1 h) and then pelleted at 3000 g. Cell pellets were resuspended in an equal volume of LB ATI and incubated (37° C., 300 rpm, 3.5 h), before being arrayed using a 96 well pin tool on LB ATI agar containing 30 μg ml$^{-1}$ 3,4-cyclohexenoesculetin-β-D-galactopyranoside (S-gal) and 50 μg ml$^{-1}$ ferric ammonium citrate.

Figure 5A:
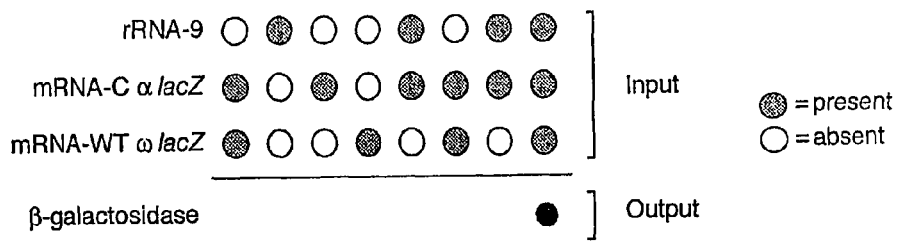

As predicted based on the measured specificities of each of these molecules, these components form an AND function in which the assembly of functional β-galactosidase is dependent on the presence of the each of the three components (FIG. 5a).

It is demonstrated herein that the selected orthogonal pairs have predictable and defined specificities with respect to the wild-type ribosome and with respect to each other. These known relationships allow the programmed synthesis of Boolean operators for the post-transcriptional regulation of gene expression, and will facilitate the synthesis of more complex Boolean networks. For example, it is possible to synthesize two of the three fundamental operators, and or, using only the ribosomes and binding sites described here. Combinations of the ribosomes reported here and other cellular components, with defined molecular specificities, should lead to sophisticated, yet programmable, post-transcriptional gene regulatory networks, for the logical synthesis of complex cellular function.

It is specifically noted that Boolean logic can come from the simultaneous use of multiple (e.g., 2 or more, 3 or more, 5 or more, 10 or more, 20 or more, etc.) orthogonal ribosome orthogonal-mRNA pairs in a single cell. To this end, mRNA-C and mRNA-A were placed upstream of two otherwise identical a fragment genes in a strain of *E. coli* expressing the ω fragment in excess. Cells were transformed with plasmid DNA encoding both rRNA-9 and rRNA-2, or one or the other mutant rRNA and a wild type rRNA. Cells were processed as described above. As predicted, each mutant rRNA led to β galactosidase activity, but cells transformed with both mutant rRNAs led to enhanced β galactosidase activity. At low β galactosidase activity thresholds, this demonstrates an OR function and at high thresholds an AND function. These experiments further demonstrate for the first time that multiple mutant rRNAs can be used to produce multiple mutant ribosome populations in the cell simultaneously, demonstrating the possibility to synthesize of logical operators composed entirely of ribosomes.

Example 5

Boolean Logic with Orthogonal Ribosomes

The network of molecular specificities of each O-ribosome, with respect to both cognate and non-cognate orthogonal ribosome binding sites on mRNA, has been defined by considering each pairwise O-ribosome•O-mRNA interaction in isolation. Pairs of O-ribosome•O-mRNA pairs have the molecular specificities that define mutual orthogonality. For example, O-ribosome-A translates its cognate O-mRNA-A, but not the non-cognate O-mRNA-C, and O-ribosome-C translates its cognate O-mRNA-C, but not the non-cognate O-mRNA-A. Similarly, O-ribosome-B•O-mRNA-B and O-ribosome-C•O-mRNA-C are mutually orthogonal (FIG. 7). (See also Rackham & Chin, 2005, J. Am. Chem. Soc. 127(50):17584-5, which is incorporated herein by reference in its entirety). In this Example it is shown that subnetworks of this network graph can be physically realized in a single cell and allow combinatorial cellular programming of entirely post-transcriptional Boolean logic functions.

The requirements for the realization of subnetworks are that multiple distinct ribosome•mRNA pairs can be produced in a single cell and that these pairs function independently of other ribosome•mRNA pairs in this context. The simultaneous expression of multiple distinct mutant ribosomes in cells has not previously been demonstrated. It requires the expression and processing of two ribosomal RNAs from two compatible plasmids. It also requires that ribosomal proteins are produced from the genome in sufficient quantities to produce functional ribosomes containing wild-type ribosomal RNA as well as two functional orthogonal ribosomes, which each contain a distinct O-rRNA.

As a first step toward the simultaneous production of three ribosomes in the cell (the wild-type ribosome and two O-ribosomes), O-rRNAs were produced from plasmids of distinct compatibility groups and the resulting ribosomes assayed for function.

Construction of Compatible rRNA Input Plasmids

The RSF rRNA expression plasmid was derived from the previously described Col E1 expression plasmid (pTrc16S23S; Rackham & Chin, 2005, Nature Chem. Biol. 1: 159-166). The RSF1030 replicon, containing a kanamycin resistance gene, was amplified by PCR from pRSFDuet-1 (Novagen) using the oligonucleotides 5'-AACTAGGGTAC-CGAATTCGGGCCTCTAAACGGGTCTTGAGG-3'(SEQ ID NO: 120) and 5'-ATTGCAGCATGCCATATGGTAACG-GAATAGCTGTTCGTTGAC-3' (SEQ ID NO: 121). The resulting PCR product was digested with Kpn I and Sph I and used to replace the Kpn I, Sph I replicon-containing portion of pTrc 16S23S ribosome plasmids. CAT activity assays for orthogonal ribosome activity were performed as described in Rackham & Chin, 2005, supra).

Construction of Logic Gate Plasmids p21, a p15A plasmid containing a cat-upp fusion was used to create the logic gate plasmids. An c) allele of lacZ (M15, deletion of amino acids 11-41) was created by performing enzymatic inverse PCR on pTrcHis2/lacZ (Invitrogen), using the following oligonucleotides 5'-GCGAGGAAAGGTCT-CATCGTCGCCCTTCCCAACAGTTGCGCAGCCTG-3' (SEQ ID NO: 122) and 5'-AGGGAGTAGGTCTCAAC-GACGTTGTAAAACGACGGGATCTATC-3' (SEQ ID NO: 123). ω fragments containing mutant ribosome binding sites were generated by PCR using this ω derivative of pTrcHis2/lacZ as a template and oligonucleotides flanking the gene. α fragment genes with altered ribosome binding sites were created by PCR with pTrcHis2/lacZ as a template. To generate AND logic gate plasmids the p21 backbone, and α fragments containing two distinct ribosome binding sites were digested and combined in a three-way ligation. To generate OR logic gates one α fragment gene was replaced by an ω fragment gene in the ligation. The plasmid maps of each resulting logic gate plasmid are included below (See "Supplementary Plasmid Maps").

Measuring Logic Function Output

The AND function was created in BW26444 cells, which are deleted in lacZ. Their genotype is (Δ(araD-araB)567, Δ(lacA-lacZ)519(::FRT), lacIp-4000(lacI$^Q$), λ$^-$, rpoS396 (Am), rph-1, Δ(rhaD-rhaB)568, hsdR514). Heat shock competent BW26444 cells containing the logic gate plasmid were prepared by standard CaCl$_2$ treatment, and combinations of rRNA inputs accessed by double transformation. Transformed cells were recovered in SOB with 2% glucose and transferred to LB agar containing 2% glucose, 50 μg ml$^{-1}$ ampicillin, 25 μg ml$^{-1}$ kanamycin, 12.5 μg ml$^{-1}$ tetracycline and incubated (16 h, 37° C.). Individual colonies were transferred to each well of a 96 well culture block containing 100 μl of media (LB containing 2% glucose, 50 μg ml$^{-1}$ ampicillin, 25 μg ml$^{-1}$ kanamycin, 12.5 μg ml$^{-1}$ tetracycline) and grown overnight. Cells were pelleted by centrifugation (3000 g, 5 min) and resuspended in 1 ml of LB containing 50 μg ml$^{-1}$ ampicillin, 25 μg ml$^{-1}$ kanamycin, 12.5 μg ml$^{-1}$ tetracycline. After a further 1 h incubation (37° C., 250 rpm) cells were supplemented with isopropyl-β-D-thiogalactopyranoside (to 1 mM), and incubated (37° C., 250 rpm, 4 h) and the OD$_{600}$ measured. Cells were pelleted at 3000 g, resuspended in 100 μL BugBuster HT (Novagen) and permealised by shaking for 25 minutes. An equal volume of 2× buffer Z (120 mM Na$_2$HPO$_4$, 80 mM NaH$_2$PO$_4$, 20 mM KCl, 2 mM MgSO$_4$, 100 mM β-mercaptoethanol) containing fluorescein di-β-D-galactopyranoside (Molecular Probes, final concentration 0.5 mM) was added and incubated (22° C.) until a strong fluorescent signal was detected (approximately 5 min). Cells and debris were pelleted and the clarified supernatant transferred to a 96 well plate. Fluorescence was detected using a Spectra Max Gemini XS (Molecular Devices), with excitation at 370 nm and emission detection at 450 nm.

Fluorescence was normalized for cell density and time of incubation with β-galactosidase substrate, using the equation:

$$\text{Fluorescence} = 1000 \times (\text{raw fluorescence}_{450\,nm}) / (t \cdot V \cdot OD_{600})$$

Where (t) is time of incubation in seconds and (V) is the volume of culture used.

The OR function was created in DH10B *E. coli*, which produce the ω fragment of β-galactosidase due to a chromosomal deletion corresponding to amino acids 11-41 within the lacZ gene. This strain has the following genotype: (F−, mcrA, Δ(mrr-hsdRMS-mcrBC), Δ(lacZ)M15, ΔlacX74, recA1, araD139, Δ(ara-leu)7697, galU, galK, rpsL(StrR), endA1, nupG). The other experimental procedures were as described above for the AND function.

One vector for rRNA production has a ColE1 origin of replication and an ampicillin resistance gene and is present at about 50 copies per cell. A second vector for rRNA production has an RSF origin of replication and a kanamycin resistance gene, and is present at about 100 copies per cell. The inventors have previously observed that the production of functional ribosomes incorporating plasmid-encoded rRNA can be strongly modulated by the sequences flanking the rRNA transcriptional cassette. To ascertain the effect of plasmid flanking sequences and plasmid copy number on the activity of the O-ribosomes incorporating plasmid-encoded rRNA, the translation of the chloramphenicol acetyl transferase gene (cat) from O-mRNA-Ccat (a version of cat with the 5' orthogonal ribosome binding site C) was measured. Cells containing RSF or ColE1 plasmids encoding rRNA-C confer resistance to chloramphenicol, with IC$_{50}$s of 250 μg mL$^{-1}$ and 150 μg mL$^{-1}$ respectively, while O-mRNA-Ccat has an IC$_{50}$ of 10 μg mL$^{-1}$ in the absence of cognate ribosome. Similar results were obtained with other O-ribosome•O-mRNA pairs. These results demonstrate that highly active orthogonal ribosomes can be produced from two compatible plasmids, and that the RSF plasmid leads to a slightly greater ribosome activity than the ColE1 plasmid, as predicted based on copy number alone.

Figure 8A:
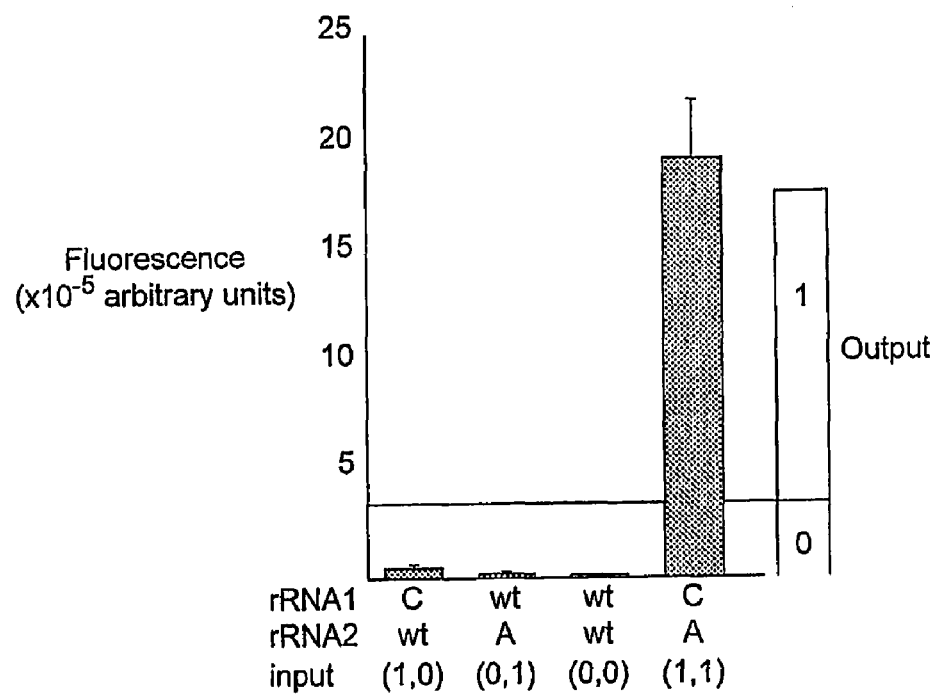
Figure 8C:
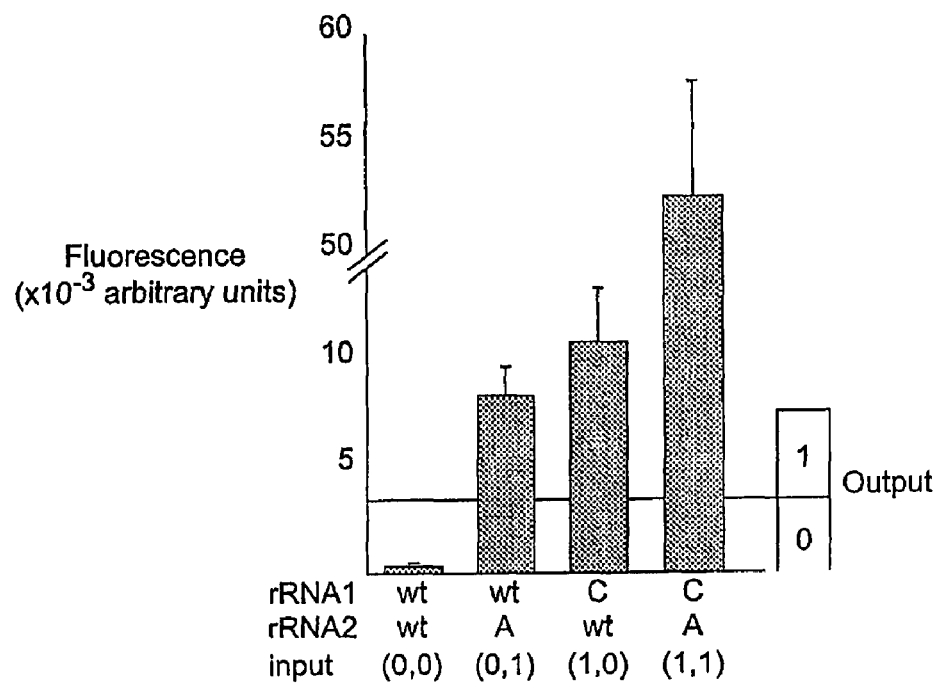
Figure 8B:
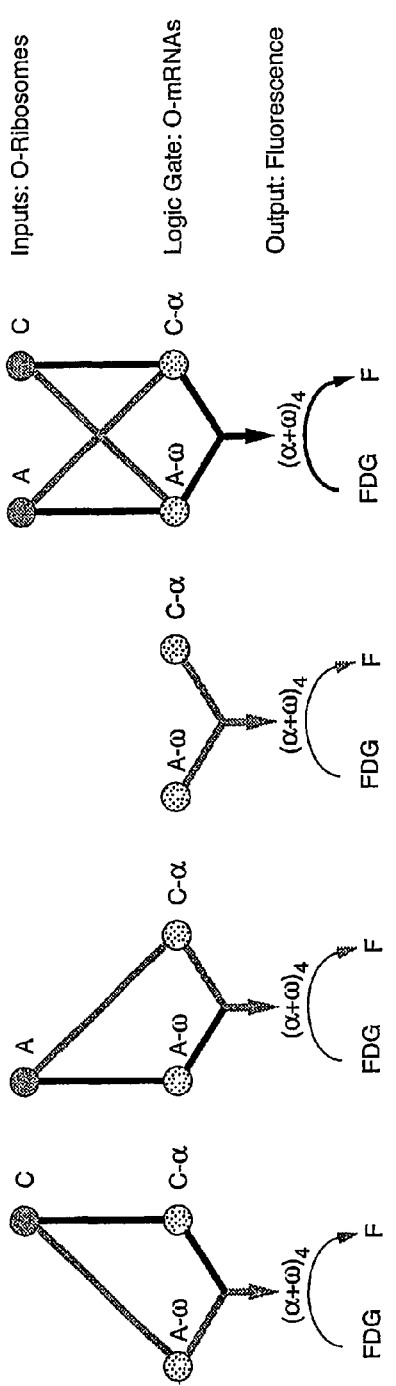
Figure 8D:
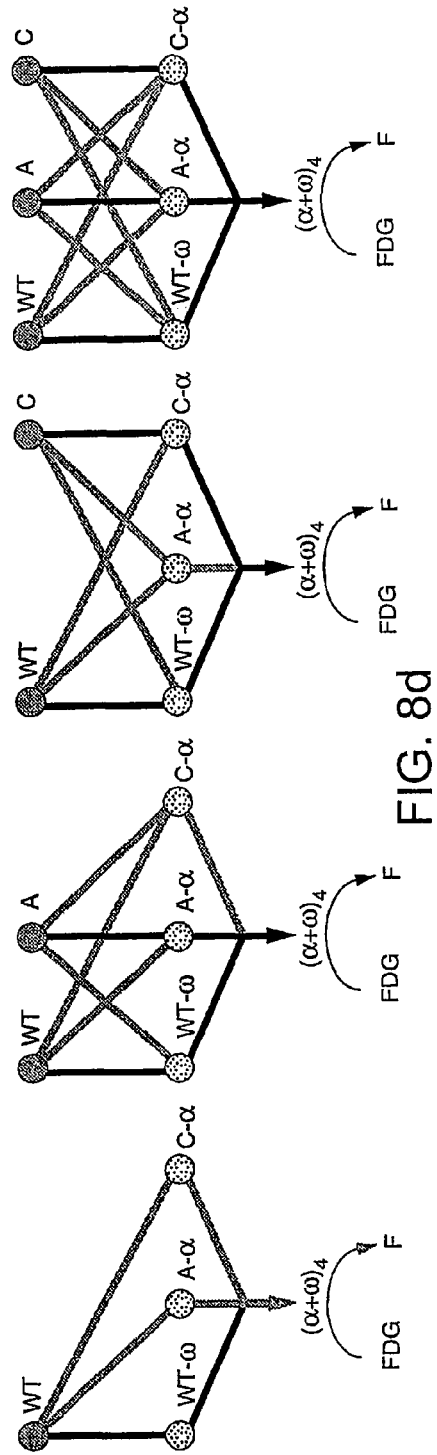

To demonstrate that multiple O-ribosomes can be produced in a single cell, and to begin to address the potential of O-ribosomes for the expression of Boolean logic, an AND gate containing O-mRNA sequences was designed. The gate is composed of two O-mRNA sequences: O-mRNA-Aω directs the synthesis of the ω fragment of (β-galactosidase, while O-mRNA-Cα directs the synthesis of the α fragment of β-galactosidase. Upon synthesis and assembly of both fragments into β-galactosidase ((α+ω)$_4$), cells hydrolyse fluorescein di-β-D-galactopyranoside (FDG) to fluorescein (F), which can be detected fluorimetrically (FIGS. 8a, b).

Cells containing a plasmid encoding both O-mRNA-Cα and O-mRNA-Aω were programmed with either wild-type rRNA, rRNA-A, rRNA-C or rRNA-C and rRNA-A together, and the conversion of FDG to fluorescein measured. Cells programmed with wild-type rRNA produce low fluorescence, which is comparable to background. This confirms that the orthogonal ribosome binding sites A and C—developed on the cat gene—are portable, and can confer orthogonality to a variety of genes. Cells programmed with rRNA-A also produce low fluorescence, as do cells programmed with rRNA-C. However cells programmed with both rRNA-A and rRNA-C give a fluorescent signal 20-fold greater than other rRNA combinations. These data demonstrate that multiple mutually orthogonal ribosomes can be functionally expressed in a single cell. Moreover they show that rRNA-A and rRNA-C can be used as inputs in a post-transcriptional AND function. Similar AND functions were also obtained with cells containing other mutually orthogonal ribosomes and their cognate O-mRNAαs and O-mRNAωs.

Next, a Boolean OR gate was created. The OR gate is composed of two O-mRNAs (O-mRNA-Aα and O-mRNA-Cα) each of which directs the synthesis of the α fragment of β-galactosidase (FIG. 8 c, d). In this system the ω fragment is constitutively produced from a wild-type ribosome binding site. Cells programmed with wild-type ribosomes produce a fluorescence comparable to that observed in the absence of plasmid-encoded a fragment. Cells programmed with rRNA-A produce a fluorescence signal 10-fold above background, while cells programmed with rRNA-C produce a level of fluorescence 15-fold above background. Cells programmed with both rRNA-C and rRNA-A give a fluorescent signal more than 50-fold above background. The increase in fluorescent signal indicates that in this system the ω-fragment is present in excess of the α-fragment though each is produced from single gene present at identical copy number and using the same promoter and terminator. When wild-type ribosome binding sites are used to replace the orthogonal ribosome binding sites on the mRNA a similar result is observed. This suggests that the mismatch in cellular concentration of ω-fragment and α-fragment result from a deficiency in either the transcription or lifetime of the α-fragment mRNA, or degradation of the α-fragment peptide. Overall, these results demonstrate that rRNA-A and rRNA-C can be used as inputs in a Boolean OR function. The OR function can also be created using other mutually orthogonal rRNAs and cognate O-mRNAs.

In conclusion, it is demonstrated that O-ribosomes and O-mRNAs can be used to create entirely post-transcriptional combinatorial logic in living cells. The Boolean gates described require multiple distinct orthogonal ribosomes as inputs and could not be assembled using the wild-type ribosome, since its removal from the cell is lethal, precluding a value of zero for its input. Demonstrated herein is how unnatural, orthogonal, modular components and a knowledge of the non-covalent interactions between components can be used to synthesize unnatural network architectures and logical functions in living matter.

Example 6

Predicting a Network of O-Ribosome O-mRNA Pairs

Amongst the three orthogonal ribosome mRNA pairs described there are nine potential ribosome mRNA interactions, most of which are of unknown, and potentially varying, strength. Calculations on genomic sequences, using Turner's rules (Freier, S. M. et al., *Proc Natl Acad Sci USA* 83, 9373-9377 (1986), Freier, S. M., Kierzek, R., Caruthers, M. H., Neilson, T. & Turner, D. H., *Biochemistry* 25, 3209-3213 (1986)), have shown that there is a signature drop in the free energy of rRNA mRNA base pairing of between 4 and 5 kcal $mol^{-1}$ for translational start sites relative to the rest of the genome (Schurr, T., Nadir, E. & Margalit, H., *Nucleic Acids Res* 21, 4019-4023 (1993), Osada, Y., Saito, R. & Tomita, M., *Bioinformatics* 15, 578-581 (1999)). Unlike genomic transcripts, the O-mRNAs described herein have a region of variable sequence surrounded by common flanking sequence, and it was reasoned that this may make their translation by O-ribosomes even more predictable. The ΔG of association was calculated for the most stable base-pairing alignment of the 3' end of mutant rRNAs and cognate and non-cognate O-mRNAs using Turner's rules. This produced calculated free energies for O-ribosome O-mRNA pairs of between 0 and 10 kcal $mol^{-1}$ (Table 2).

TABLE 2

The predicted and measured specificities of orthogonal ribosomes on cognate- and non-cognate-orthogonal ribosome binding sites.

| | O-mRNA | | | | | | | | |
| --- | --- | --- | --- | --- | --- | --- | --- | --- | --- |
| O-Ribo- | B | | | A | | | C | | |
| some | $\Delta G^a$ | $\Delta \Delta G^b$ | $IC_{50}{}^c$ | $\Delta G^a$ | $\Delta \Delta G^b$ | $IC_{50}{}^c$ | $\Delta G^a$ | $\Delta \Delta G^b$ | $IC_{50}{}^c$ |
| 9 | −1.5 | −7.5 | 10 | −2.9 | −6 | 10 | −9.0 | 0 | 150 |
| 2 | −6.3 | −2.7 | 50 | −8.9 | 0 | 200 | −2.9 | −6.1 | 10 |
| 8 | −9.0 | 0 | 150 | −2.1 | −6.8 | 10 | −0.7 | −8.3 | 10 |

$^a$ΔG (kcal $mol^{-1}$) calculated for the base pairing interaction using Turner's rules.
$^b$ΔΔG = $\Delta G_{[cognate\ site]}$ − $\Delta G_{[non-cognate\ site]}$.
$^c$$IC_{50}$ (μg $ml^{-1}$) of chloramphenicol resistance.

Figure 5B:
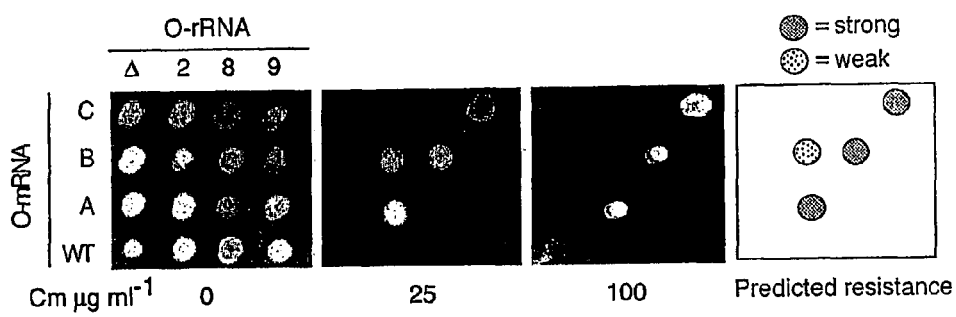
Figure 5C:
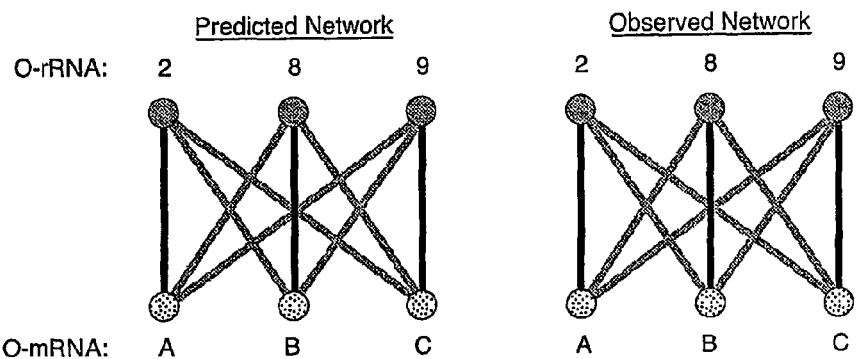

Cells were then transformed with all combinations of O-ribosomes and O-mRNAs and measured the chloramphenicol resistance generated from the O-cat-upp reporters (FIG. 5b). From the free energy values and $IC_{50}$ values a predicted- and an experimental-network graph was generated, in which the lines representing the interactions between O-ribosomes and O-mRNAs have a grey scale value between 0 and 100 that corresponds linearly with the predicted free energy of base-pairing or the $IC_{50}$ value of Chloramphenicol resistance respectively (FIG. 5c). The correlation between the predicted network of interaction strengths and the observed network is striking. To calculate a simple measure of the upper limit of the likelihood of predicting the correct network graph by chance a simple case in which the nine ribosome mRNA interactions are digitized was considered. There are 512 ($2^9$) distinct ways in which three ribosomes can interact with three mRNAs. Each of these solutions describes a specific network of interactions, and can be represented by a unique network graph. The upper limit of likelihood that free energy calculations could correctly predict all nine interactions in the graph is therefore 1 in 512.

As suggested by the free energy calculations, it was found that ribosomes containing rRNA-9 function with mRNA-C, but not mRNA-A or mRNA-B, ribosomes containing rRNA-8 function with mRNA-B, but not with mRNA-A or mRNA-C, and ribosomes containing rRNA-2 function with mRNA-A and also with mRNA-B. It is interesting to note that the free energy calculations predict that the rRNA-2 mRNA-B interaction will be weaker than the rRNA-2 mRNA-A pair interaction and a corresponding difference is seen in the experimental $IC_{50}$ values. The C9 ribosome mRNA pair is mutually orthogonal with the A2 ribosome mRNA pair, and mutually orthogonal with the B8 ribosome mRNA pair. Ribosomes bearing rRNA-8 are orthogonal to the mRNA-A, but ribosomes bearing rRNA-2 function with mRNA-B. Moreover, comparison of the aligned sequences of rRNA-2 mRNA-B and rRNA-8 mRNA-A pairs provides a molecular basis for their different behavior. The rRNA-2 mRNA-B pair contains two G-U base-pairs, that stabilize the interaction. However the corresponding A-C mismatches in the rRNA-8 mRNA-A pair are destabilizing. The stability of the G-U pair breaks the symmetry of interactions predicted based on Watson-Crick base pair interactions and provides a mechanism by which functional connections between ribosomes and mRNAs in a synthetic network can become asymmetric.

OTHER EMBODIMENTS

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

APPENDIX 1

Oligonucleotides Used in the Described Examples

| Name | Sequence (5'-3') | Purpose |
| --- | --- | --- |
| 16SClaXhoF | GAATTTATCGATACTCGAGGCCGCTGAGAAAAAGCGAAGC (SEQ ID NO: 12) | Creating Xho I site 5' of 16S gene |
| 16SXbaR | TGGGCCTCTAGACGAAGGGGACACGAAAATTG (SEQ ID NO: 13) | Amplification of 16S in combination with 16SClaXhoF |

APPENDIX 1-continued

Oligonucleotides Used in the Described Examples

| Name | Sequence (5'-3') | Purpose |
|---|---|---|
| 72MCSnoBsaF | GATGATATCAGATCTGCCGCTCTCCCTATAGT GAGTC (SEQ ID NO: 14) | Mutation of Bsa I site in MCS of pSP72 in combination with 72MCSnoBsaR |
| 72MCSnoBsaR | GACTCACTATAGGGAGAGCGGCAGATCTGAT ATCATC (SEQ ID NO: 15) | Mutation of Bsa I site in MCS of pSP72 in combination with 72MCSnoBsaF |
| 73MCSnoBsaF | CTTCAGCTGCTCGAGGCCGCTCTCCCTATAGT GAGTCG (SEQ ID NO: 16) | Mutation of Bsa I site in MCS of pSP73 in combination with 73MCSnoBsaR |
| 73MCSnoBsaR | CGACTCACTATAGGGAGAGCGGCCTCGAGCA GCTGAAG (SEQ ID NO: 17) | Mutation of Bsa I site in MCS of pSP73 in combination with 73MCSnoBsaF |
| SPampnoBsaF | GGAGCCGGTGAGCGTGGCTCTCGCGGTATCA TTG (SEQ ID NO: 18) | Mutation of Bsa I site in AmpR gene of pSP72/73 in combination with SPampnoBsaR |
| SPampnoBsaR | CAATGATACCGCGAGAGCCACGCTCACCGGC TCC (SEQ ID NO: 19) | Mutation of Bsa I site in AmpR gene of pSP72/73 in combination with SPampnoBsaF |
| minusPstIF | CTGAAGCTTGCATGCCCGCAGGTCGACTCTA G (SEQ ID NO: 20) | Mutation of Pst I site in MCS of pSP72/73 in combination with minusPsIR |
| minusPstIR | CTAGAGTCGACCTGCGGGCATGCAAGCTTCA G (SEQ ID NO: 21) | Mutation of Pst I site in MCS of pSP72/73 in combination with minusPstIF |
| 23SnoBsaAUf | CTGGGGCGGTCACCTCCTAAAGAGTAACGGA GGTGCACGAAGGTTG (SEQ ID NO: 22) | Mutation of Bsa I site in 23S rRNA gene in combination with 23SnoBsaAUr |
| 23SnoBsaAUr | CAACCTTCGTGCACCTCCGTTACTCTTTAGGA GGTGACCGCCCCAG (SEQ ID NO: 23) | Mutation of Bsa I site in 23S rRNA gene in combination with 23SnoBsaAUf |
| 5SnoBsaC2Uf | GATGGTAGTGTGGGGTTTCCCCATGCGAGAG TAG (SEQ ID NO: 24) | Mutation of Bsa I site in 5S rRNA gene in combination with 5SnoBsaC2Ur |
| 5SnoBsaC2Ur | CTACTCTCGCATGGGGAAACCCCACACTACC ATC (SEQ ID NO: 25) | Mutation of Bsa I site in 5S rRNA gene in combination with 5SnoBsaC2Uf |
| pBR322SeqF | TGTCTGCTCCCGGCATCCGCTTACAG (SEQ ID NO: 26) | For amplification of minimal pTrc promoter in combination with TrcpromR |
| TrcpromR | ATTCCGCTCGAGTGCCCACACAGATTGTCTG ATAAATTG (SEQ ID NO: 27) | For amplification of minimal pTrc promoter in combination with pBR322SeqF |
| KanF | CAGTAACTCGAGCGGCCGCATGAGCCATATT CAACGGGAAACGTCTTGTTCGAGGCCGGGAT TAAATTC (SEQ ID NO: 28) | For amplification of KanR gene in combination with KanR |
| KanR | GCTTTGGAATTCCCGGGAATCGATGGTACCA GATCTGGATCCTCCGGCGTTCAGCCTGTG (SEQ ID NO: 29) | For amplification of KanR gene in combination with KanF |
| AmpNgoMIVF | GAGTTGCTCTTGGCCGGCGTCAATACGGGAT AATAC (SEQ ID NO: 30) | For introduction of NgoM IV site in AmpR gene of pSP72/73 in combination with AmpNgoMIVR |
| AmpNgoMIVR | GTATTATCCCGTATTGACGCCGGCCAAGAGC AACTC (SEQ ID NO: 31) | For introduction of NgoM IV site in AmpR gene of pSP72/73 in combination with AmpNgoMIVF |
| SDlibF | GGAAAGGTCTCAGGTTGGATCANNNNNNTAC CTTAAAGAAGCGTACTTTGTAG (SEQ ID NO: 31) | For randomization of anti-SD in 16S rRNA gene in combination with SDlibR |

APPENDIX 1-continued

Oligonucleotides Used in the Described Examples

| Name | Sequence (5'-3') | Purpose |
|---|---|---|
| SD1libR | GAGTAGGTCTCAAACCGCAGGTTCCCCTACG (SEQ ID NO: 33) | For randomization of anti-SD in 16S rRNA gene in combination with SD1libF |
| SD2libF | GGAAAGGTCTCAGAATACCGNNGGCGAAGG CGGCCCCTGGACGAA (SEQ ID NO: 34) | For randomization of 722, 723 in 16S rRNA gene in combination with SD2libR |
| SD2libR | GAGTAGGTCTCAATTCCTCCAGATCTCTACGC ATTTCAC (SEQ ID NO: 35) | For randomization of 722, 723 in 16S rRNA gene in combination with SD2libF |
| RBSlib7F | GGGAAAGGTCTCCCGCTTTCANNNNNNNCCG CAAATGGAGAAAAAAATCACTGGATATACC (SEQ ID NO: 36) | For randomization of RBS in p21 in combination with RBSlib7R |
| RBSrev | GGAGTAGGTCTCAAGCGGCCGCTTCCACACA TTAAACTAGTTC (SEQ ID NO: 37) | For randomization of RBS in p21 in combination with RBSlib7F |
| wtRBSnoATGf | GCGCAGGAAAGGTGTCAGCCGCTTTGAGGAG GCTCGAGAACCCGAGAAAAAAATCACTGGAT ATACCACCG (SEQ ID NO: 38) | Mutation of AUG start codon of cat-upp gene in p21 to CCC in combination with wtRBSrev |
| wtRBSrev | GCGCAGAGTAGGTCTCACGGCCGCTTTCCACA CATTAAACTAGTTCG (SEQ ID NO: 39) | Mutation of AUG start codon of cat-upp gene in p21 to CCC in combination with wtRBSnoATGf |
| wtRBSfwd | GCGCAGGAAAGGTCTCAGCCGCTTTCAGGAG GCTCGAGAAATGGAGAAAAAAATCACTGGA TATACCACC (SEQ ID NO: 40) | Deletion of promotor of cat-upp gene in p21 in combination with noPROMrev |
| noPROMrev | GCGCAGAGTAGGTCTCACGGCAGGGCCCTAC GTGCCGATCAACGTCTC (SEQ ID NO: 41) | Deletion of promotor of cat-upp gene in p21 in combination with wtRBSfwd |
| RSFfwd | AACTAGGGTACCGAATTCGGGCCTCTAAACG GGTCTTGAGG (SEQ ID NO: 42) | Amplification of RSF ori and KanR gene fragment from pRSFDuet-1 in combination with RSFrev |
| RSFrev | ATTGCAGCATGCCATATGGTAACGGAATAGC TGTTCGTTGAC (SEQ ID NO: 43) | Amplification of RSF ori and KanR gene fragment from pRSFDuet-1 in combination with RSFfwd |
| ACYCNotfwd | ATGAAAGCGGCCGCTTCCACACATTAAACTA GTTCG (SEQ ID NO: 44) | Amplification of p21 backbone fragment in combination with ACYCBglrev |
| ACYCBglrev | GGTACAGAGATCTAGAATTCGAAGCTTGGGCC CGAACA (SEQ ID NO: 45) | Amplification of p21 backbone fragment in combination with ACYCNotfwd |
| G9alphaF | GTGGAAGCGGCCGCTTTCATATCCCTCCGCA AATGCCCGTCGTTTTACAACGTCGTGAC (SEQ ID NO: 45) | Amplification of alpha complementing lacZ gene fragment with G9 RBS in combination with alphaR |
| alphaR | TTGACAAGATCTGAATTCCCATGGATAAAAC GAAAGGCCCAGTCTTTCGACTGAGCCTTTCG TTTTATTTGTTAATCGTAACCGTGCATCTGC CAG (SEQ ID NO: 47) | Amplification of alpha complementing lacZ gene fragment with G9 RBS in combination with G9alphaF |

The invention claimed is:

1. A method of selecting an orthogonal mRNA orthogonal rRNA pair, the method comprising:
   a) providing a first library encoding mRNA molecules, the individual mRNA members encoded by which comprise a sequence coding for a fusion polypeptide, said fusion polypeptide comprising a positive selectable marker polypeptide and a negative selectable marker polypeptide, wherein for individual members of said first library, said sequence coding for a fusion polypeptide is operably linked to one of a plurality of mutated ribosome binding sites;
   b) providing a second library encoding mutant rRNA molecules, the individual members of which are mutated in a region comprising sequence that interacts with mRNA at the ribosome binding site;
   c) introducing said first library to cells and performing a negative selection against mRNA molecules encoded by said first library that are substrates for wild-type ribosomes, thereby selecting members of said first library that encode mRNAs that are not substrates for wild-type ribosomes;
   d) introducing said second library encoding mutant rRNA molecules into cells comprising said first library members selected in step (c), and performing a positive selection for those cells expressing said positive selectable marker, whereby an orthogonal mRNA orthogonal rRNA pair comprising a first library member encoding an mRNA that is efficiently translated by a ribosome comprising an rRNA mutant encoded by second library is identified.

2. The method of claim 1 wherein said negative selectable marker comprises a uracil phosphoribosyltransferase coding sequence.

3. The method of claim 2 wherein said performing a negative selection comprises contacting cells with 5-fluorouracil.

4. The method of claim 1 wherein said positive selectable marker comprises an antibiotic resistance coding sequence.

5. The method of claim 4 wherein said antibiotic resistance gene encodes chloramphenicol acetyltransferase.

6. The method of claim 1 wherein performing a positive selection comprises contacting said cells with an antibiotic.

7. The method of claim 6 wherein said antibiotic comprises chloramphenicol.

8. The method of claim 1 wherein said fusion polypeptide comprises chloramphenicol acetyltransferase fused to uracil phosphoribosyltransferase.

9. The method of claim 8 wherein said uracil phosphoribosyltransferase is fused C-terminal to said chloramphenicol acetyltransferase.

10. The method of claim 1 wherein members of said first library encoding mRNA molecules are diversified in sequence between −13 and +1 relative to an AUG initiation codon at the start of said sequence coding for a fusion polypeptide.

11. The method of claim 1 wherein members of said first library encoding mRNA molecules are diversified in sequence between −7 and −13 relative to an AUG initiation codon at the start of said sequence coding for a fusion polypeptide.

12. The method of claim 1 wherein members of said second library encode mutant 16S rRNAs.

* * * * *

SEQUENCE LISTING

<160> NUMBER OF SEQ ID NOS: 129

<210> SEQ ID NO 1
<211> LENGTH: 5
<212> TYPE: RNA
<213> ORGANISM: Escherichia coli

<400> SEQUENCE: 1 ggagg                                                                        5

<210> SEQ ID NO 2
<211> LENGTH: 5
<212> TYPE: RNA
<213> ORGANISM: Escherichia coli

<400> SEQUENCE: 2 ccucc                                                                        5

<210> SEQ ID NO 3
<211> LENGTH: 61
<212> TYPE: DNA
<213> ORGANISM: artificial sequence
<220> FEATURE:
<223> OTHER INFORMATION: Mutagenic PCR primer
<220> FEATURE:
<221> NAME/KEY: misc_feature
<222> LOCATION: (22)..(28)
<223> OTHER INFORMATION: n = G, A, T or C

<400> SEQUENCE: 3
gggaaaggtc tcccgctttc annnnnnncc gcaaatggag aaaaaaatca ctggatatac      60
c                                                                           61

<210> SEQ ID NO 4
<211> LENGTH: 43
<212> TYPE: DNA
<213> ORGANISM: artificial sequence
<220> FEATURE:
<223> OTHER INFORMATION: Reverse PCR primer for mutagenesis

<400> SEQUENCE: 4
ggagtaggtc tcaagcggcc gcttccacac attaaactag ttc                             43

<210> SEQ ID NO 5
<211> LENGTH: 53
<212> TYPE: DNA
<213> ORGANISM: artificial sequence
<220> FEATURE:
<223> OTHER INFORMATION: Mutagenic PCR primer
<220> FEATURE:
<221> NAME/KEY: misc_feature
<222> LOCATION: (23)..(28)
<223> OTHER INFORMATION: n = G, A, T, or C.

<400> SEQUENCE: 5
ggaaaggtct caggttggat cannnnnnta ccttaaagaa gcgtactttg tag                  53

<210> SEQ ID NO 6
<211> LENGTH: 31
<212> TYPE: DNA
<213> ORGANISM: artificial sequence
<220> FEATURE:
<223> OTHER INFORMATION: Reverse PCR primer for mutagenesis

<400> SEQUENCE: 6
gagtaggtct caaaccgcag gttcccctac g         31

<210> SEQ ID NO 7
<211> LENGTH: 46
<212> TYPE: DNA
<213> ORGANISM: artificial sequence
<220> FEATURE:
<223> OTHER INFORMATION: Mutagenic PCR primer
<220> FEATURE:
<221> NAME/KEY: misc_feature
<222> LOCATION: (21)..(22)
<223> OTHER INFORMATION: n = G, A, T or C

<400> SEQUENCE: 7
ggaaaggtct cagaataccg nnggcgaagg cggccccctg gacgaa         46

<210> SEQ ID NO 8
<211> LENGTH: 39
<212> TYPE: DNA
<213> ORGANISM: artificial sequence
<220> FEATURE:
<223> OTHER INFORMATION: Reverse PCR primer for mutagenesis

<400> SEQUENCE: 8
gagtaggtct caattcctcc agatctctac gcatttcac         39

<210> SEQ ID NO 9
<211> LENGTH: 5
<212> TYPE: RNA
<213> ORGANISM: artificial sequence
<220> FEATURE:
<223> OTHER INFORMATION: Selected cognate ribosome mRNA sequence

<400> SEQUENCE: 9 accac         5

<210> SEQ ID NO 10
<211> LENGTH: 5
<212> TYPE: RNA
<213> ORGANISM: artificial sequence
<220> FEATURE:
<223> OTHER INFORMATION: Selected cognate ribosome mRNA sequence

<400> SEQUENCE: 10 acugc         5

<210> SEQ ID NO 11
<211> LENGTH: 5
<212> TYPE: RNA
<213> ORGANISM: artificial sequence
<220> FEATURE:
<223> OTHER INFORMATION: Selected cognate ribosome mRNA sequence

<400> SEQUENCE: 11 auccc         5

<210> SEQ ID NO 12
<211> LENGTH: 40
<212> TYPE: DNA
<213> ORGANISM: artificial sequence
<220> FEATURE:
<223> OTHER INFORMATION: cloning oligonucleotide

<400> SEQUENCE: 12
gaatttatcg atactcgagg ccgctgagaa aaagcgaagc         40

<210> SEQ ID NO 13
<211> LENGTH: 32
<212> TYPE: DNA
<213> ORGANISM: artificial sequence
<220> FEATURE:
<223> OTHER INFORMATION: Cloning oligonucleotide

<400> SEQUENCE: 13
tgggcctcta gacgaagggg acacgaaaat tg                          32

<210> SEQ ID NO 14
<211> LENGTH: 37
<212> TYPE: DNA
<213> ORGANISM: artificial sequence
<220> FEATURE:
<223> OTHER INFORMATION: Cloning oligonucleotide

<400> SEQUENCE: 14
gatgatatca gatctgccgc tctccctata gtgagtc                     37

<210> SEQ ID NO 15
<211> LENGTH: 37
<212> TYPE: DNA
<213> ORGANISM: artificial sequence
<220> FEATURE:
<223> OTHER INFORMATION: Cloning oligonucleotide

<400> SEQUENCE: 15
gactcactat agggagagcg gcagatctga tatcatc                     37

<210> SEQ ID NO 16
<211> LENGTH: 38
<212> TYPE: DNA
<213> ORGANISM: artificial sequence
<220> FEATURE:
<223> OTHER INFORMATION: Cloning oligonucleotide

<400> SEQUENCE: 16
cttcagctgc tcgaggccgc tctccctata gtgagtcg                    38

<210> SEQ ID NO 17
<211> LENGTH: 38
<212> TYPE: DNA
<213> ORGANISM: artificial sequence
<220> FEATURE:
<223> OTHER INFORMATION: Cloning oligonucleotide

<400> SEQUENCE: 17
cgactcacta tagggagagc ggcctcgagc agctgaag                    38

<210> SEQ ID NO 18
<211> LENGTH: 34
<212> TYPE: DNA
<213> ORGANISM: artificial sequence
<220> FEATURE:
<223> OTHER INFORMATION: Cloning oligonucleotide

<400> SEQUENCE: 18
ggagccggtg agcgtggctc tcgcggtatc attg                        34

<210> SEQ ID NO 19
<211> LENGTH: 34
<212> TYPE: DNA
<213> ORGANISM: artificial sequence
<220> FEATURE:
<223> OTHER INFORMATION: Cloning oligonucleotide

<400> SEQUENCE: 19
caatgatacc gcgagagcca cgctcaccgg ctcc                                34

<210> SEQ ID NO 20
<211> LENGTH: 32
<212> TYPE: DNA
<213> ORGANISM: artificial sequence
<220> FEATURE:
<223> OTHER INFORMATION: Cloning oligonucleotide

<400> SEQUENCE: 20
ctgaagcttg catgcccgca ggtcgactct ag                                  32

<210> SEQ ID NO 21
<211> LENGTH: 32
<212> TYPE: DNA
<213> ORGANISM: artificial sequence
<220> FEATURE:
<223> OTHER INFORMATION: Cloning oligonucleotide

<400> SEQUENCE: 21
ctagagtcga cctgcgggca tgcaagcttc ag                                  32

<210> SEQ ID NO 22
<211> LENGTH: 46
<212> TYPE: DNA
<213> ORGANISM: artificial sequence
<220> FEATURE:
<223> OTHER INFORMATION: Cloning oligonucleotide

<400> SEQUENCE: 22
ctggggcggt cacctcctaa agagtaacgg aggtgcacga aggttg                   46

<210> SEQ ID NO 23
<211> LENGTH: 46
<212> TYPE: DNA
<213> ORGANISM: artificial sequence
<220> FEATURE:
<223> OTHER INFORMATION: Cloning oligonucleotide

<400> SEQUENCE: 23
caaccttcgt gcacctccgt tactctttag gaggtgaccg ccccag                   46

<210> SEQ ID NO 24
<211> LENGTH: 34
<212> TYPE: DNA
<213> ORGANISM: artificial sequence
<220> FEATURE:
<223> OTHER INFORMATION: Cloning oligonucleotide

<400> SEQUENCE: 24
gatggtagtg tggggtttcc ccatgcgaga gtag                                34

<210> SEQ ID NO 25
<211> LENGTH: 34
<212> TYPE: DNA
<213> ORGANISM: artificial sequence
<220> FEATURE:
<223> OTHER INFORMATION: Cloning oligonucleotide

<400> SEQUENCE: 25
ctactctcgc atggggaaac cccacactac catc                                34

<210> SEQ ID NO 26

```
<211> LENGTH: 26
<212> TYPE: DNA
<213> ORGANISM: artificial sequence
<220> FEATURE:
<223> OTHER INFORMATION: Cloning oligonucleotide

<400> SEQUENCE: 26
tgtctgctcc cggcatccgc ttacag                                           26

<210> SEQ ID NO 27
<211> LENGTH: 38
<212> TYPE: DNA
<213> ORGANISM: artificial sequence
<220> FEATURE:
<223> OTHER INFORMATION: Cloning oligonucleotide

<400> SEQUENCE: 27
attccgctcg agtgcccaca cagattgtct gataaatt                              38

<210> SEQ ID NO 28
<211> LENGTH: 69
<212> TYPE: DNA
<213> ORGANISM: artificial sequence
<220> FEATURE:
<223> OTHER INFORMATION: Cloning oligonucleotide

<400> SEQUENCE: 28
cagtaactcg agcggccgca tgagccatat tcaacgggaa acgtcttgtt cgaggccgcg      60
attaaattc                                                              69

<210> SEQ ID NO 29
<211> LENGTH: 60
<212> TYPE: DNA
<213> ORGANISM: artificial sequence
<220> FEATURE:
<223> OTHER INFORMATION: Cloning oligonucleotide

<400> SEQUENCE: 29
gctttggaat tcccgggaat cgatggtacc agatctggat cctccggcgt tcagcctgtg      60

<210> SEQ ID NO 30
<211> LENGTH: 36
<212> TYPE: DNA
<213> ORGANISM: artificial sequence
<220> FEATURE:
<223> OTHER INFORMATION: Cloning oligonucleotide

<400> SEQUENCE: 30
gagttgctct tggccggcgt caatacggga taatac                                36

<210> SEQ ID NO 31
<211> LENGTH: 36
<212> TYPE: DNA
<213> ORGANISM: artificial sequence
<220> FEATURE:
<223> OTHER INFORMATION: Cloning oligonucleotide

<400> SEQUENCE: 31
gtattatccc gtattgacgc cggccaagag caactc                                36

<210> SEQ ID NO 32
<211> LENGTH: 53
<212> TYPE: DNA
<213> ORGANISM: artificial sequence
<220> FEATURE:
<223> OTHER INFORMATION: Cloning oligonucleotide
```

```
<220> FEATURE:
<221> NAME/KEY: misc_feature
<222> LOCATION: (23)..(28)
<223> OTHER INFORMATION: n = G, A, T or C

<400> SEQUENCE: 32
ggaaaggtct caggttggat cannnnnnta ccttaaagaa gcgtactttg tag          53

<210> SEQ ID NO 33
<211> LENGTH: 31
<212> TYPE: DNA
<213> ORGANISM: artificial sequence
<220> FEATURE:
<223> OTHER INFORMATION: Cloning oligonucleotide

<400> SEQUENCE: 33
gagtaggtct caaaccgcag gttcccctac g                                   31

<210> SEQ ID NO 34
<211> LENGTH: 46
<212> TYPE: DNA
<213> ORGANISM: artificial sequence
<220> FEATURE:
<223> OTHER INFORMATION: Mutagenic cloning oligonucleotide
<220> FEATURE:
<221> NAME/KEY: misc_feature
<222> LOCATION: (21)..(22)
<223> OTHER INFORMATION: n = G, A, T or C

<400> SEQUENCE: 34
ggaaaggtct cagaataccg nnggcgaagg cggcccccctg gacgaa                  46

<210> SEQ ID NO 35
<211> LENGTH: 39
<212> TYPE: DNA
<213> ORGANISM: artificial sequence
<220> FEATURE:
<223> OTHER INFORMATION: Mutagenic cloning oligonucleotide

<400> SEQUENCE: 35
gagtaggtct caattcctcc agatctctac gcatttcac                           39

<210> SEQ ID NO 36
<211> LENGTH: 61
<212> TYPE: DNA
<213> ORGANISM: artificial sequence
<220> FEATURE:
<223> OTHER INFORMATION: Mutagenic cloning oligonucleotide
<220> FEATURE:
<221> NAME/KEY: misc_feature
<222> LOCATION: (22)..(28)
<223> OTHER INFORMATION: n = G, A, T or C

<400> SEQUENCE: 36
gggaaaggtc tcccgctttc annnnnnncc gcaaatggag aaaaaaatca ctggatatac    60
c                                                                    61

<210> SEQ ID NO 37
<211> LENGTH: 43
<212> TYPE: DNA
<213> ORGANISM: artificial organism
<220> FEATURE:
<223> OTHER INFORMATION: Cloning oligonucleotide

<400> SEQUENCE: 37
ggagtaggtc tcaagcggcc gcttccacac attaaactag ttc                      43
```

<210> SEQ ID NO 38
<211> LENGTH: 71
<212> TYPE: DNA
<213> ORGANISM: artificial sequence
<220> FEATURE:
<223> OTHER INFORMATION: Cloning oligonucleotide

<400> SEQUENCE: 38
gcgcaggaaa ggtctcagcc gctttcagga ggctcgagaa cccgagaaaa aaatcactgg    60
ataTaccacc g                                                        71

<210> SEQ ID NO 39
<211> LENGTH: 46
<212> TYPE: DNA
<213> ORGANISM: artificial organism
<220> FEATURE:
<223> OTHER INFORMATION: Cloning oligonucleotide

<400> SEQUENCE: 39
gcgcagagta ggtctcacgg ccgcttccac acattaaact agttcg                  46

<210> SEQ ID NO 40
<211> LENGTH: 70
<212> TYPE: DNA
<213> ORGANISM: Artificial sequence
<220> FEATURE:
<223> OTHER INFORMATION: Cloning oligonucleotide

<400> SEQUENCE: 40
gcgcaggaaa ggtctcagcc gctttcagga ggctcgagaa atggagaaaa aaatcactgg    60
ataTaccacc                                                          70

<210> SEQ ID NO 41
<211> LENGTH: 48
<212> TYPE: DNA
<213> ORGANISM: artificial sequence
<220> FEATURE:
<223> OTHER INFORMATION: Cloning oligonucleotide

<400> SEQUENCE: 41
gcgcagagta ggtctcacgg cagggcccta cgtgccgatc aacgtctc                48

<210> SEQ ID NO 42
<211> LENGTH: 41
<212> TYPE: DNA
<213> ORGANISM: Artificial sequence
<220> FEATURE:
<223> OTHER INFORMATION: Cloning oligonucleotide

<400> SEQUENCE: 42
aactagggta ccgaattcgg gcctctaaac gggtcttgag g                       41

<210> SEQ ID NO 43
<211> LENGTH: 42
<212> TYPE: DNA
<213> ORGANISM: Artificial sequence
<220> FEATURE:
<223> OTHER INFORMATION: Cloning oligonucleotide

<400> SEQUENCE: 43
attgcagcat gccatatggt aacggaatag ctgttcgttg ac                      42

<210> SEQ ID NO 44
<211> LENGTH: 36

```
<212> TYPE: DNA
<213> ORGANISM: Artificial sequence
<220> FEATURE:
<223> OTHER INFORMATION: Cloning oligonucleotide

<400> SEQUENCE: 44
atgaaagcgg ccgcttccac acattaaact agttcg                                36

<210> SEQ ID NO 45
<211> LENGTH: 37
<212> TYPE: DNA
<213> ORGANISM: artificial sequence
<220> FEATURE:
<223> OTHER INFORMATION: Cloning oligonucleotide

<400> SEQUENCE: 45
ggtacgagat ctagaattcg aagcttgggc ccgaaca                               37

<210> SEQ ID NO 46
<211> LENGTH: 59
<212> TYPE: DNA
<213> ORGANISM: Artificial sequence
<220> FEATURE:
<223> OTHER INFORMATION: Cloning oligonucleotide

<400> SEQUENCE: 46
gtggaagcgg ccgctttcat atccctccgc aaatgcccgt cgttttacaa cgtcgtgac      59

<210> SEQ ID NO 47
<211> LENGTH: 96
<212> TYPE: DNA
<213> ORGANISM: Artificial sequence
<220> FEATURE:
<223> OTHER INFORMATION: Cloning oligonucleotide

<400> SEQUENCE: 47
ttgacaagat ctgaattccc atggataaaa cgaaaggccc agtctttcga ctgagccttt     60
cgttttattt gttaatcgta accgtgcatc tgccag                               96

<210> SEQ ID NO 48
<211> LENGTH: 6
<212> TYPE: RNA
<213> ORGANISM: artificial sequence
<220> FEATURE:
<223> OTHER INFORMATION: selected orthogonal mRNA sequence

<400> SEQUENCE: 48 caccac                                                                 6

<210> SEQ ID NO 49
<211> LENGTH: 7
<212> TYPE: RNA
<213> ORGANISM: artificial sequence
<220> FEATURE:
<223> OTHER INFORMATION: Selected orthogonal mRNA sequence

<400> SEQUENCE: 49 caacugc                                                                7

<210> SEQ ID NO 50
<211> LENGTH: 7
<212> TYPE: RNA
<213> ORGANISM: artificial sequence
<220> FEATURE:
<223> OTHER INFORMATION: Selected orthogonal mRNA sequence
```

```
<400> SEQUENCE: 50 caucccu                                                          7

<210> SEQ ID NO 51
<211> LENGTH: 5
<212> TYPE: RNA
<213> ORGANISM: artificial sequence
<220> FEATURE:
<223> OTHER INFORMATION: Selected orthogonal mRNA sequence

<400> SEQUENCE: 51 ucccu                                                            5

<210> SEQ ID NO 52
<211> LENGTH: 12
<212> TYPE: RNA
<213> ORGANISM: artificial sequence
<220> FEATURE:
<223> OTHER INFORMATION: Selected orthogonal mRNA sequence

<400> SEQUENCE: 52
caccacccgc aa                                                   12

<210> SEQ ID NO 53
<211> LENGTH: 13
<212> TYPE: RNA
<213> ORGANISM: artificial sequence
<220> FEATURE:
<223> OTHER INFORMATION: Selected orthogonal mRNA sequence

<400> SEQUENCE: 53
caacugcccg caa                                                  13

<210> SEQ ID NO 54
<211> LENGTH: 13
<212> TYPE: RNA
<213> ORGANISM: artificial sequence
<220> FEATURE:
<223> OTHER INFORMATION: Selected orthogonal mRNA sequence

<400> SEQUENCE: 54
caucccuccg caa                                                  13

<210> SEQ ID NO 55
<211> LENGTH: 11
<212> TYPE: RNA
<213> ORGANISM: artificial sequence
<220> FEATURE:
<223> OTHER INFORMATION: Selected orthogonal mRNA sequence

<400> SEQUENCE: 55
ucccuccgca a                                                    11

<210> SEQ ID NO 56
<211> LENGTH: 6
<212> TYPE: RNA
<213> ORGANISM: artificial sequence
<220> FEATURE:
<223> OTHER INFORMATION: orthogonal 16S rRNA sequence

<400> SEQUENCE: 56 aguggu                                                           6

<210> SEQ ID NO 57
<211> LENGTH: 6
```

```
<212> TYPE: RNA
<213> ORGANISM: artificial sequence
<220> FEATURE:
<223> OTHER INFORMATION: orthogonal 16S rRNA sequence

<400> SEQUENCE: 57 cugugg                                                                    6

<210> SEQ ID NO 58
<211> LENGTH: 6
<212> TYPE: RNA
<213> ORGANISM: artificial sequence
<220> FEATURE:
<223> OTHER INFORMATION: orthogonal 16S rRNA sequence

<400> SEQUENCE: 58 uugugg                                                                    6

<210> SEQ ID NO 59
<211> LENGTH: 6
<212> TYPE: RNA
<213> ORGANISM: artificial sequence
<220> FEATURE:
<223> OTHER INFORMATION: orthogonal 16S rRNA sequence

<400> SEQUENCE: 59 uugugg                                                                    6

<210> SEQ ID NO 60
<211> LENGTH: 6
<212> TYPE: RNA
<213> ORGANISM: artificial sequence
<220> FEATURE:
<223> OTHER INFORMATION: orthogonal 16S rRNA sequence

<400> SEQUENCE: 60 augcag                                                                    6

<210> SEQ ID NO 61
<211> LENGTH: 6
<212> TYPE: RNA
<213> ORGANISM: artificial sequence
<220> FEATURE:
<223> OTHER INFORMATION: orthogonal 16S rRNA sequence

<400> SEQUENCE: 61 uugcag                                                                    6

<210> SEQ ID NO 62
<211> LENGTH: 6
<212> TYPE: RNA
<213> ORGANISM: artificial sequence
<220> FEATURE:
<223> OTHER INFORMATION: orthogonal 16S rRNA sequence

<400> SEQUENCE: 62 ucgcag                                                                    6

<210> SEQ ID NO 63
<211> LENGTH: 6
<212> TYPE: RNA
<213> ORGANISM: artificial sequence
<220> FEATURE:
<223> OTHER INFORMATION: orthogonal 16S rRNA sequence

<400> SEQUENCE: 63
```

-continued

```
ccgcag                                                          6

<210> SEQ ID NO 64
<211> LENGTH: 6
<212> TYPE: RNA
<213> ORGANISM: artificial sequence
<220> FEATURE:
<223> OTHER INFORMATION: orthogonal 16S rRNA sequence

<400> SEQUENCE: 64 ugggau                                                          6

<210> SEQ ID NO 65
<211> LENGTH: 6
<212> TYPE: RNA
<213> ORGANISM: artificial sequence
<220> FEATURE:
<223> OTHER INFORMATION: orthogonal 16S rRNA sequence

<400> SEQUENCE: 65 ugggau                                                          6

<210> SEQ ID NO 66
<211> LENGTH: 9
<212> TYPE: RNA
<213> ORGANISM: artificial sequence
<220> FEATURE:
<223> OTHER INFORMATION: orthogonal 16S rRNA sequence

<400> SEQUENCE: 66 ccgaguggc                                                       9

<210> SEQ ID NO 67
<211> LENGTH: 12
<212> TYPE: RNA
<213> ORGANISM: artificial sequence
<220> FEATURE:
<223> OTHER INFORMATION: orthogonal 16S rRNA sequence

<400> SEQUENCE: 67
aucaaguggu ua                                                  12

<210> SEQ ID NO 68
<211> LENGTH: 9
<212> TYPE: RNA
<213> ORGANISM: artificial sequence
<220> FEATURE:
<223> OTHER INFORMATION: orthogonal 16S rRNA sequence

<400> SEQUENCE: 68 ccgcguggc                                                       9

<210> SEQ ID NO 69
<211> LENGTH: 12
<212> TYPE: RNA
<213> ORGANISM: artificial sequence
<220> FEATURE:
<223> OTHER INFORMATION: orthogonal 16S rRNA sequence

<400> SEQUENCE: 69
aucacugugg ua                                                  12

<210> SEQ ID NO 70
<211> LENGTH: 9
<212> TYPE: RNA
<213> ORGANISM: artificial sequence
```

```
<220> FEATURE:
<223> OTHER INFORMATION: orthogonal 16S rRNA sequence

<400> SEQUENCE: 70 ccgcauggc                                                                9

<210> SEQ ID NO 71
<211> LENGTH: 12
<212> TYPE: RNA
<213> ORGANISM: artificial sequence
<220> FEATURE:
<223> OTHER INFORMATION: orthogonal 16S rRNA sequence

<400> SEQUENCE: 71
aucauugugg ua                                                           12

<210> SEQ ID NO 72
<211> LENGTH: 9
<212> TYPE: RNA
<213> ORGANISM: artificial sequence
<220> FEATURE:
<223> OTHER INFORMATION: orthogonal 16S rRNA sequence

<400> SEQUENCE: 72 ccgguuggc                                                                9

<210> SEQ ID NO 73
<211> LENGTH: 12
<212> TYPE: RNA
<213> ORGANISM: artificial sequence
<220> FEATURE:
<223> OTHER INFORMATION: orthogonal 16S rRNA sequence

<400> SEQUENCE: 73
aucauugugg ua                                                           12

<210> SEQ ID NO 74
<211> LENGTH: 9
<212> TYPE: RNA
<213> ORGANISM: artificial sequence
<220> FEATURE:
<223> OTHER INFORMATION: orthogonal 16S rRNA sequence

<400> SEQUENCE: 74 ccgacuggc                                                                9

<210> SEQ ID NO 75
<211> LENGTH: 12
<212> TYPE: RNA
<213> ORGANISM: artificial sequence
<220> FEATURE:
<223> OTHER INFORMATION: orthogonal 16S rRNA sequence

<400> SEQUENCE: 75
aucaaugcag ua                                                           12

<210> SEQ ID NO 76
<211> LENGTH: 9
<212> TYPE: RNA
<213> ORGANISM: artificial sequence
<220> FEATURE:
<223> OTHER INFORMATION: orthogonal 16S rRNA sequence

<400> SEQUENCE: 76 ccgacuggc                                                                9
```

```
<210> SEQ ID NO 77
<211> LENGTH: 12
<212> TYPE: RNA
<213> ORGANISM: artificial sequence
<220> FEATURE:
<223> OTHER INFORMATION: orthogonal 16S rRNA sequence

<400> SEQUENCE: 77
aucauugcag ua                                                            12

<210> SEQ ID NO 78
<211> LENGTH: 9
<212> TYPE: RNA
<213> ORGANISM: artificial sequence
<220> FEATURE:
<223> OTHER INFORMATION: orthogonal 16S rRNA sequence

<400> SEQUENCE: 78 ccgcguggc                                                                 9

<210> SEQ ID NO 79
<211> LENGTH: 12
<212> TYPE: RNA
<213> ORGANISM: artificial sequence
<220> FEATURE:
<223> OTHER INFORMATION: orthogonal 16S rRNA sequence

<400> SEQUENCE: 79
aucaucgcag ua                                                            12

<210> SEQ ID NO 80
<211> LENGTH: 9
<212> TYPE: RNA
<213> ORGANISM: Artificial sequence
<220> FEATURE:
<223> OTHER INFORMATION: orthogonal 16S rRNA sequence

<400> SEQUENCE: 80 ccgcauggc                                                                 9

<210> SEQ ID NO 81
<211> LENGTH: 12
<212> TYPE: RNA
<213> ORGANISM: artificial sequence
<220> FEATURE:
<223> OTHER INFORMATION: orthogonal 16S rRNA sequence

<400> SEQUENCE: 81
aucaccgcag ua                                                            12

<210> SEQ ID NO 82
<211> LENGTH: 12
<212> TYPE: RNA
<213> ORGANISM: artificial sequence
<220> FEATURE:
<223> OTHER INFORMATION: orthogonal 16S rRNA sequence

<400> SEQUENCE: 82
aucaugggau ua                                                            12

<210> SEQ ID NO 83
<211> LENGTH: 9
<212> TYPE: RNA
<213> ORGANISM: artificial sequence
<220> FEATURE:
<223> OTHER INFORMATION: orthogonal 16S rRNA sequence
```

```
<400> SEQUENCE: 83 ccgguuggc                                                                  9

<210> SEQ ID NO 84
<211> LENGTH: 6
<212> TYPE: RNA
<213> ORGANISM: artificial sequence
<220> FEATURE:
<223> OTHER INFORMATION: selected orthogonal mRNA sequence

<400> SEQUENCE: 84 caccac                                                                     6

<210> SEQ ID NO 85
<211> LENGTH: 6
<212> TYPE: RNA
<213> ORGANISM: artificial sequence
<220> FEATURE:
<223> OTHER INFORMATION: Selected orthogonal 16S rRNA sequence

<400> SEQUENCE: 85 aguggu                                                                     6

<210> SEQ ID NO 86
<211> LENGTH: 6
<212> TYPE: RNA
<213> ORGANISM: artificial sequence
<220> FEATURE:
<223> OTHER INFORMATION: Selected orthogonal 16S rRNA sequence

<400> SEQUENCE: 86 cugugg                                                                     6

<210> SEQ ID NO 87
<211> LENGTH: 6
<212> TYPE: RNA
<213> ORGANISM: artificial sequence
<220> FEATURE:
<223> OTHER INFORMATION: Selected orthogonal 16S rRNA sequence

<400> SEQUENCE: 87 uugugg                                                                     6

<210> SEQ ID NO 88
<211> LENGTH: 7
<212> TYPE: RNA
<213> ORGANISM: artificial sequence
<220> FEATURE:
<223> OTHER INFORMATION: Selected orthogonal 16S rRNA sequence

<400> SEQUENCE: 88 caacugc                                                                    7

<210> SEQ ID NO 89
<211> LENGTH: 6
<212> TYPE: RNA
<213> ORGANISM: artificial sequence
<220> FEATURE:
<223> OTHER INFORMATION: Selected orthogonal 16S rRNA sequence

<400> SEQUENCE: 89 augcag                                                                     6

<210> SEQ ID NO 90
```

```
<211> LENGTH: 6
<212> TYPE: RNA
<213> ORGANISM: artificial sequence
<220> FEATURE:
<223> OTHER INFORMATION: Selected orthogonal 16S rRNA sequence

<400> SEQUENCE: 90 uugcag                                                                  6

<210> SEQ ID NO 91
<211> LENGTH: 6
<212> TYPE: RNA
<213> ORGANISM: artificial sequence
<220> FEATURE:
<223> OTHER INFORMATION: Selected orthogonal 16S rRNA sequence

<400> SEQUENCE: 91 ucgcag                                                                  6

<210> SEQ ID NO 92
<211> LENGTH: 6
<212> TYPE: RNA
<213> ORGANISM: artificial sequence
<220> FEATURE:
<223> OTHER INFORMATION: Selected orthogonal 16S rRNA sequence

<400> SEQUENCE: 92 ccgcag                                                                  6

<210> SEQ ID NO 93
<211> LENGTH: 7
<212> TYPE: RNA
<213> ORGANISM: artificial sequence
<220> FEATURE:
<223> OTHER INFORMATION: Selected orthogonal mRNA sequence

<400> SEQUENCE: 93 caucccu                                                                 7

<210> SEQ ID NO 94
<211> LENGTH: 6
<212> TYPE: RNA
<213> ORGANISM: artificial sequence
<220> FEATURE:
<223> OTHER INFORMATION: Selected orthogonal 16S rRNA sequence

<400> SEQUENCE: 94 ugggau                                                                  6

<210> SEQ ID NO 95
<211> LENGTH: 12
<212> TYPE: RNA
<213> ORGANISM: artificial sequence
<220> FEATURE:
<223> OTHER INFORMATION: Selected orthogonal mRNA sequence

<400> SEQUENCE: 95
caccacccgc aa                                                          12

<210> SEQ ID NO 96
<211> LENGTH: 8
<212> TYPE: RNA
<213> ORGANISM: artificial sequence
<220> FEATURE:
<223> OTHER INFORMATION: Selected orthogonal 16S rRNA sequence

<400> SEQUENCE: 96
```

```
ccgagggc                                                          8
```

<210> SEQ ID NO 97
<211> LENGTH: 12
<212> TYPE: RNA
<213> ORGANISM: artificial sequence
<220> FEATURE:
<223> OTHER INFORMATION: Selected orthogonal 16S rRNA sequence

<400> SEQUENCE: 97

```
aucaaguggu ua                                                    12
```

<210> SEQ ID NO 98
<211> LENGTH: 8
<212> TYPE: RNA
<213> ORGANISM: artificial sequence
<220> FEATURE:
<223> OTHER INFORMATION: Selected orthogonal 16S rRNA sequence

<400> SEQUENCE: 98

```
ccgcgggc                                                          8
```

<210> SEQ ID NO 99
<211> LENGTH: 12
<212> TYPE: RNA
<213> ORGANISM: artificial sequence
<220> FEATURE:
<223> OTHER INFORMATION: Selected orthogonal 16S rRNA sequence

<400> SEQUENCE: 99

```
aucacugugg ua                                                    12
```

<210> SEQ ID NO 100
<211> LENGTH: 8
<212> TYPE: RNA
<213> ORGANISM: artificial sequence
<220> FEATURE:
<223> OTHER INFORMATION: Selected orthogonal 16S rRNA sequence

<400> SEQUENCE: 100

```
ccgcaggc                                                          8
```

<210> SEQ ID NO 101
<211> LENGTH: 12
<212> TYPE: RNA
<213> ORGANISM: artificial sequence
<220> FEATURE:
<223> OTHER INFORMATION: Selected orthogonal 16S rRNA sequence

<400> SEQUENCE: 101

```
aucauugugg ua                                                    12
```

<210> SEQ ID NO 102
<211> LENGTH: 8
<212> TYPE: RNA
<213> ORGANISM: artificial sequence
<220> FEATURE:
<223> OTHER INFORMATION: Selected orthogonal 16S rRNA sequence

<400> SEQUENCE: 102

```
ccgguggc                                                          8
```

<210> SEQ ID NO 103
<211> LENGTH: 13
<212> TYPE: RNA

```
<213> ORGANISM: artificial sequence
<220> FEATURE:
<223> OTHER INFORMATION: Selected orthogonal mRNA sequence

<400> SEQUENCE: 103
caacugcccg caa                                                            13

<210> SEQ ID NO 104
<211> LENGTH: 8
<212> TYPE: RNA
<213> ORGANISM: artificial sequence
<220> FEATURE:
<223> OTHER INFORMATION: Selected orthogonal 16S rRNA sequence

<400> SEQUENCE: 104 ccgacggc                                                                   8

<210> SEQ ID NO 105
<211> LENGTH: 12
<212> TYPE: RNA
<213> ORGANISM: artificial sequence
<220> FEATURE:
<223> OTHER INFORMATION: Selected orthogoanl 16S rRNA sequence

<400> SEQUENCE: 105
aucaaugcag ua                                                             12

<210> SEQ ID NO 106
<211> LENGTH: 12
<212> TYPE: RNA
<213> ORGANISM: artificial sequence
<220> FEATURE:
<223> OTHER INFORMATION: Selected orthogonal 16S rRNA sequence

<400> SEQUENCE: 106
aucauugcag ua                                                             12

<210> SEQ ID NO 107
<211> LENGTH: 8
<212> TYPE: RNA
<213> ORGANISM: artificial sequence
<220> FEATURE:
<223> OTHER INFORMATION: Selected orthogonal 16S rRNA sequence

<400> SEQUENCE: 107 ccgcgggc                                                                   8

<210> SEQ ID NO 108
<211> LENGTH: 12
<212> TYPE: RNA
<213> ORGANISM: artificial sequence
<220> FEATURE:
<223> OTHER INFORMATION: Selected orthogonal 16S rRNA sequence

<400> SEQUENCE: 108
aucaucgcag ua                                                             12

<210> SEQ ID NO 109
<211> LENGTH: 8
<212> TYPE: RNA
<213> ORGANISM: artificial sequence
<220> FEATURE:
<223> OTHER INFORMATION: Selected orthogonal 16S rRNA sequence

<400> SEQUENCE: 109 ccgcaggc                                                                   8
```

<210> SEQ ID NO 110
<211> LENGTH: 12
<212> TYPE: RNA
<213> ORGANISM: artificial sequence
<220> FEATURE:
<223> OTHER INFORMATION: Selected orthogonal 16S rRNA sequence

<400> SEQUENCE: 110
aucaccgcag ua                                                          12

<210> SEQ ID NO 111
<211> LENGTH: 13
<212> TYPE: RNA
<213> ORGANISM: artificial sequence
<220> FEATURE:
<223> OTHER INFORMATION: Selected orthogonal mRNA sequence

<400> SEQUENCE: 111
caucccuccg caa                                                         13

<210> SEQ ID NO 112
<211> LENGTH: 12
<212> TYPE: RNA
<213> ORGANISM: artificial sequence
<220> FEATURE:
<223> OTHER INFORMATION: Selected orthogonal 16S rRNA sequence

<400> SEQUENCE: 112
aucaugggau ua                                                          12

<210> SEQ ID NO 113
<211> LENGTH: 8
<212> TYPE: RNA
<213> ORGANISM: artificial sequence
<220> FEATURE:
<223> OTHER INFORMATION: Selected orthogonal 16S rRNA sequence

<400> SEQUENCE: 113 ccguggc                                                                 8

<210> SEQ ID NO 114
<211> LENGTH: 21
<212> TYPE: RNA
<213> ORGANISM: Escherichia coli

<400> SEQUENCE: 114
uuucauagga ggccgcaaau g                                                21

<210> SEQ ID NO 115
<211> LENGTH: 8
<212> TYPE: RNA
<213> ORGANISM: Escherichia coli

<400> SEQUENCE: 115 ccguggc                                                                 8

<210> SEQ ID NO 116
<211> LENGTH: 12
<212> TYPE: RNA
<213> ORGANISM: Escherichia coli

<400> SEQUENCE: 116
aucaccuccu ua                                                          12

<210> SEQ ID NO 117
<211> LENGTH: 21
<212> TYPE: RNA
<213> ORGANISM: artificial sequence
<220> FEATURE:
<223> OTHER INFORMATION: randomized mRNA sequence for library
      generation
<220> FEATURE:
<221> NAME/KEY: misc_feature
<222> LOCATION: (6)..(12)
<223> OTHER INFORMATION: n = G, A, U or C

<400> SEQUENCE: 117
uuucannnnn nnccgcaaau g                                              21

<210> SEQ ID NO 118
<211> LENGTH: 8
<212> TYPE: RNA
<213> ORGANISM: artificial sequence
<220> FEATURE:
<223> OTHER INFORMATION: 16S rRNA sequence mutated to generate
      library
<220> FEATURE:
<221> NAME/KEY: misc_feature
<222> LOCATION: (4)..(5)
<223> OTHER INFORMATION: n = G, A, C, or U

<400> SEQUENCE: 118 ccgnnggc                                                              8

<210> SEQ ID NO 119
<211> LENGTH: 12
<212> TYPE: RNA
<213> ORGANISM: artificial sequence
<220> FEATURE:
<223> OTHER INFORMATION: 16S rRNA sequence mutated to form library
<220> FEATURE:
<221> NAME/KEY: misc_feature
<222> LOCATION: (5)..(10)
<223> OTHER INFORMATION: n = G, A, C, or U

<400> SEQUENCE: 119
aucannnnnn ua                                                        12

<210> SEQ ID NO 120
<211> LENGTH: 40
<212> TYPE: DNA
<213> ORGANISM: artificial sequence
<220> FEATURE:
<223> OTHER INFORMATION: Cloning oligonucleotide

<400> SEQUENCE: 120
aactagggta ccgaattcgg gcctctaaac gggtcttgag                          40

<210> SEQ ID NO 121
<211> LENGTH: 42
<212> TYPE: DNA
<213> ORGANISM: artificial sequence
<220> FEATURE:
<223> OTHER INFORMATION: Cloning oligonucleotide

<400> SEQUENCE: 121
attgcagcat gccatatggt aacggaatag ctgttcgttg ac                       42

<210> SEQ ID NO 122
<211> LENGTH: 47
<212> TYPE: DNA
<213> ORGANISM: artificial sequence

```
<220> FEATURE:
<223> OTHER INFORMATION: Cloning oligonucleotide

<400> SEQUENCE: 122
gcgaggaaag gtctcatcgt cgcccttccc aacagttgcg cagcctg          47

<210> SEQ ID NO 123
<211> LENGTH: 43
<212> TYPE: DNA
<213> ORGANISM: artificial sequence
<220> FEATURE:
<223> OTHER INFORMATION: Cloning oligonucleotide

<400> SEQUENCE: 123
agggagtagg tctcaacgac gttgtaaaac gacgggatct atc              43

<210> SEQ ID NO 124
<211> LENGTH: 20
<212> TYPE: RNA
<213> ORGANISM: artificial sequence
<220> FEATURE:
<223> OTHER INFORMATION: Orthologous mRNA-A

<400> SEQUENCE: 124
uuucacacca cccgcaaaug                                        20

<210> SEQ ID NO 125
<211> LENGTH: 12
<212> TYPE: RNA
<213> ORGANISM: artificial sequence
<220> FEATURE:
<223> OTHER INFORMATION: Orthologous rRNA-A

<400> SEQUENCE: 125
aucacugugg ua                                                12

<210> SEQ ID NO 126
<211> LENGTH: 21
<212> TYPE: RNA
<213> ORGANISM: artificial sequence
<220> FEATURE:
<223> OTHER INFORMATION: Orthologous mRNA-B

<400> SEQUENCE: 126
uuucacaacu gcccgcaaau g                                      21

<210> SEQ ID NO 127
<211> LENGTH: 12
<212> TYPE: RNA
<213> ORGANISM: artificial sequence
<220> FEATURE:
<223> OTHER INFORMATION: Orthologous rRNA-B

<400> SEQUENCE: 127
aucaccgcag ua                                                12

<210> SEQ ID NO 128
<211> LENGTH: 21
<212> TYPE: RNA
<213> ORGANISM: artificial sequence
<220> FEATURE:
<223> OTHER INFORMATION: Orthologous mRNA-C

<400> SEQUENCE: 128
uuucacaucc cuccgcaaau g                                      21
```

```
<210> SEQ ID NO 129
<211> LENGTH: 12
<212> TYPE: RNA
<213> ORGANISM: artificial sequence
<220> FEATURE:
<223> OTHER INFORMATION: Orthologous rRNA-C

<400> SEQUENCE: 129 aucauggau ua                                                          12
```